United States Patent
Tabata et al.

(10) Patent No.: US 11,583,163 B2
(45) Date of Patent: Feb. 21, 2023

(54) ENDOSCOPE SYSTEM FOR ADJUSTING RATIO OF DISTRIBUTING PRIMARY LIGHT TO FIRST ILLUMINATOR AND SECOND ILLUMINATOR

(71) Applicant: OLYMPUS CORPORATION, Tokyo (JP)

(72) Inventors: Motoki Tabata, Hino (JP); Bakusui Daidoji, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 267 days.

(21) Appl. No.: 16/791,025

(22) Filed: Feb. 14, 2020

(65) Prior Publication Data

US 2020/0178781 A1 Jun. 11, 2020

Related U.S. Application Data

(63) Continuation of application No. PCT/JP2017/032702, filed on Sep. 11, 2017.

(51) Int. Cl.
*A61B 1/00* (2006.01)
*A61B 1/06* (2006.01)
*A61B 1/07* (2006.01)

(52) U.S. Cl.
CPC ........ *A61B 1/00006* (2013.01); *A61B 1/0002* (2013.01); *A61B 1/00009* (2013.01); *A61B 1/06* (2013.01); *A61B 1/063* (2013.01); *A61B 1/0607* (2013.01); *A61B 1/0646* (2013.01);
(Continued)

(58) Field of Classification Search
None
See application file for complete search history.

(56) References Cited

U.S. PATENT DOCUMENTS

| | | | | |
|---|---|---|---|---|
| 6,800,057 B2 * | 10/2004 | Tsujita | ............... | A61B 1/00009 600/109 |
| 7,043,291 B2 * | 5/2006 | Sendai | ................... | A61B 1/045 600/160 |
| 8,000,776 B2 * | 8/2011 | Gono | ................... | A61B 1/0638 600/476 |

(Continued)

FOREIGN PATENT DOCUMENTS

| | | |
|---|---|---|
| JP | 2002-112959 A | 4/2002 |
| JP | 5959768 B2 | 8/2016 |

OTHER PUBLICATIONS

Japanese Office Action dated Oct. 13, 2020 in Japanese Patent Application No. 2019-540736.
(Continued)

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

An endoscope system includes: a light source that is configured to emit primary light; plural illuminators that are configured to be irradiated with the primary light to emit plural respective illumination light generated based on the radiated primary light toward an observation object so that at least part of the plural illumination light overlap on the observation object; and an adjuster that is configured to desirably adjust a ratio of light quantities of the primary light that travels from the light source to the respective illuminators, so as to distribute the primary light to the respective illuminators.

18 Claims, 21 Drawing Sheets

(52) U.S. Cl.
CPC .......... *A61B 1/0655* (2022.02); *A61B 1/0669* (2013.01); *A61B 1/0684* (2013.01); *A61B 1/07* (2013.01)

(56) References Cited

U.S. PATENT DOCUMENTS

| | | | | |
|---|---|---|---|---|
| 8,295,917 | B2* | 10/2012 | Ishihara | A61B 1/043 600/477 |
| 8,721,532 | B2* | 5/2014 | Takei | G01N 21/6456 600/180 |
| 2002/0035330 | A1* | 3/2002 | Cline | A61B 1/0638 600/476 |
| 2006/0241349 | A1* | 10/2006 | Gono | A61B 1/0638 600/160 |
| 2007/0112256 | A1 | 5/2007 | Terakawa et al. | |
| 2009/0036743 | A1* | 2/2009 | Yabe | A61B 5/0071 600/180 |
| 2010/0049058 | A1* | 2/2010 | Ishihara | A61B 1/05 600/477 |
| 2011/0071352 | A1* | 3/2011 | Ozawa | A61B 1/063 600/109 |
| 2013/0096376 | A1* | 4/2013 | Takei | A61B 1/063 600/103 |
| 2013/0329224 | A1 | 12/2013 | Takaoka et al. | |
| 2017/0000314 | A1 | 1/2017 | Honda | |

OTHER PUBLICATIONS

Japanese Office Action dated Apr. 20, 2021 received in 2019-540736.
English translation of International Preliminary Report on Patentability dated Mar. 17, 2020, together with the Written Opinion issued in International Application No. PCT/JP2017/032702.
International Search Report dated Nov. 21, 2017 issued in PCT/JP2017/032702.

* cited by examiner

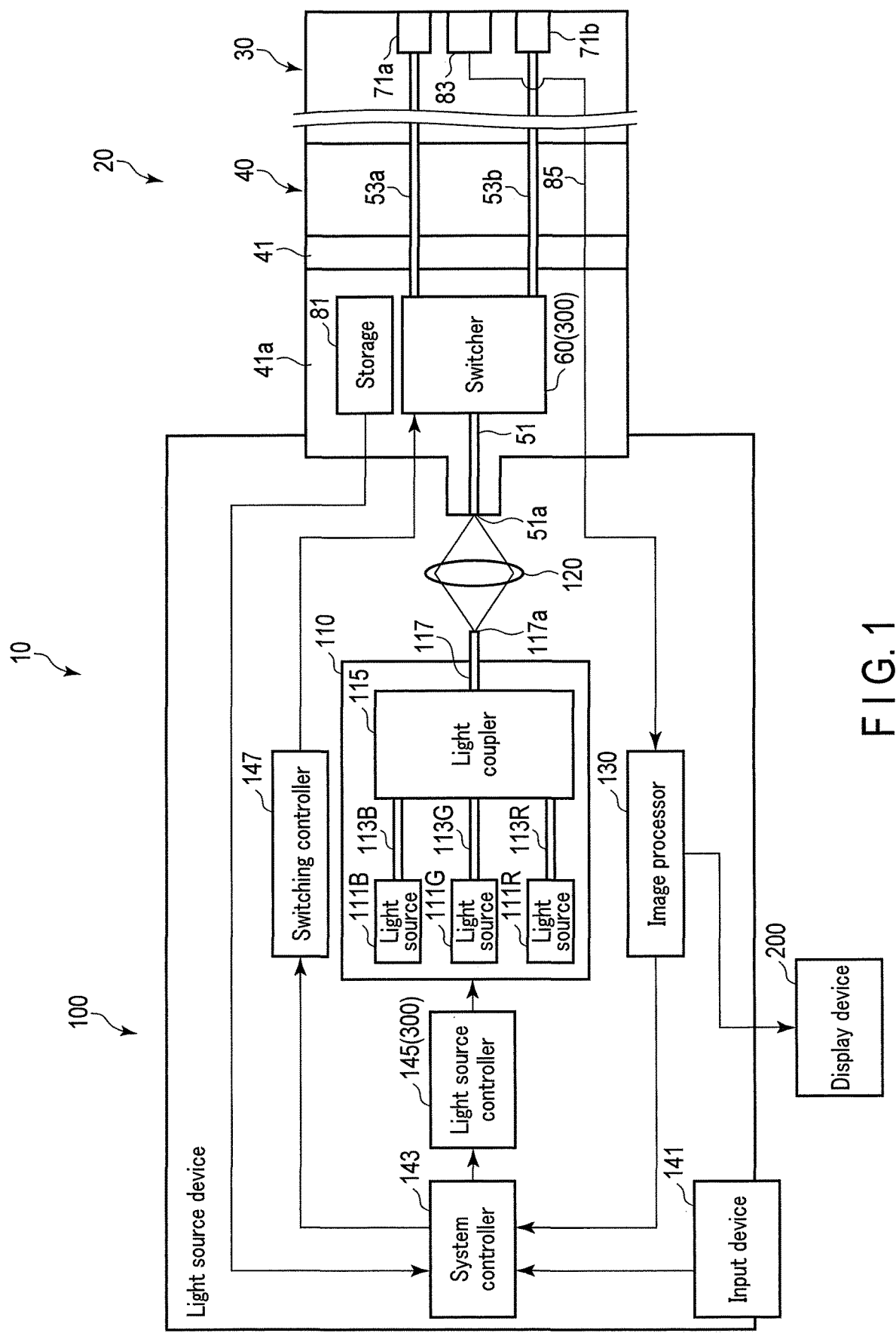
F I G. 1

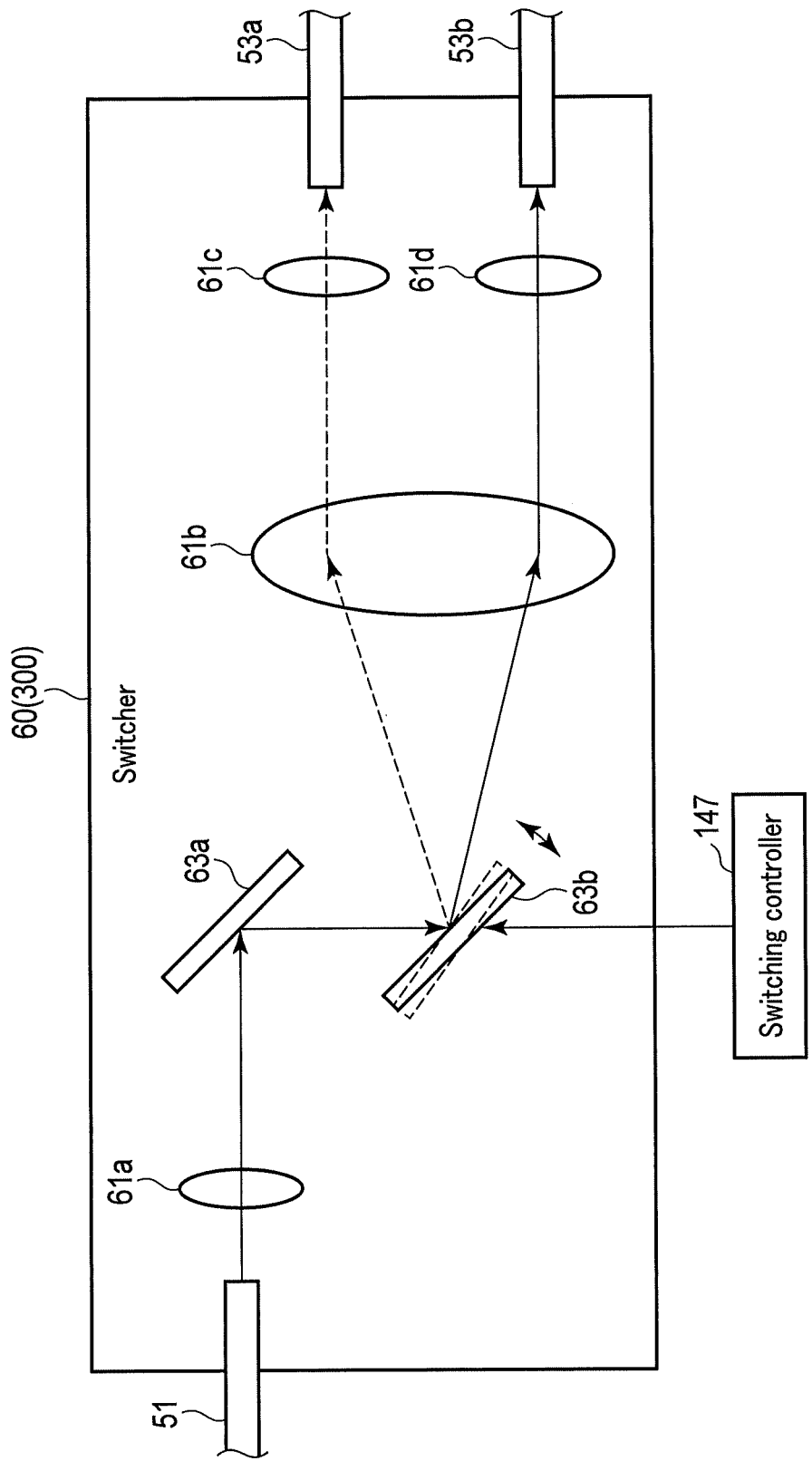
F I G. 2

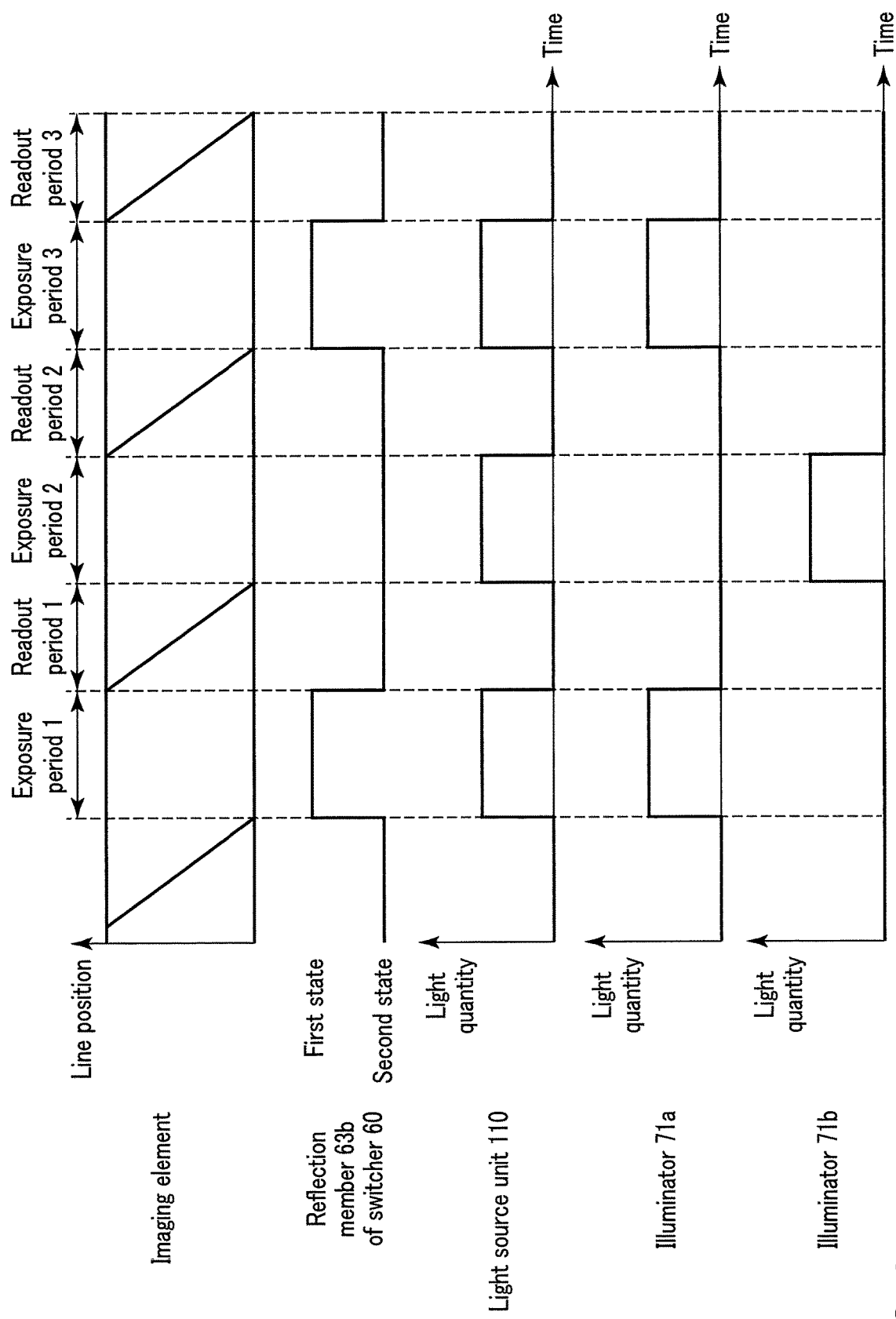
F I G. 3

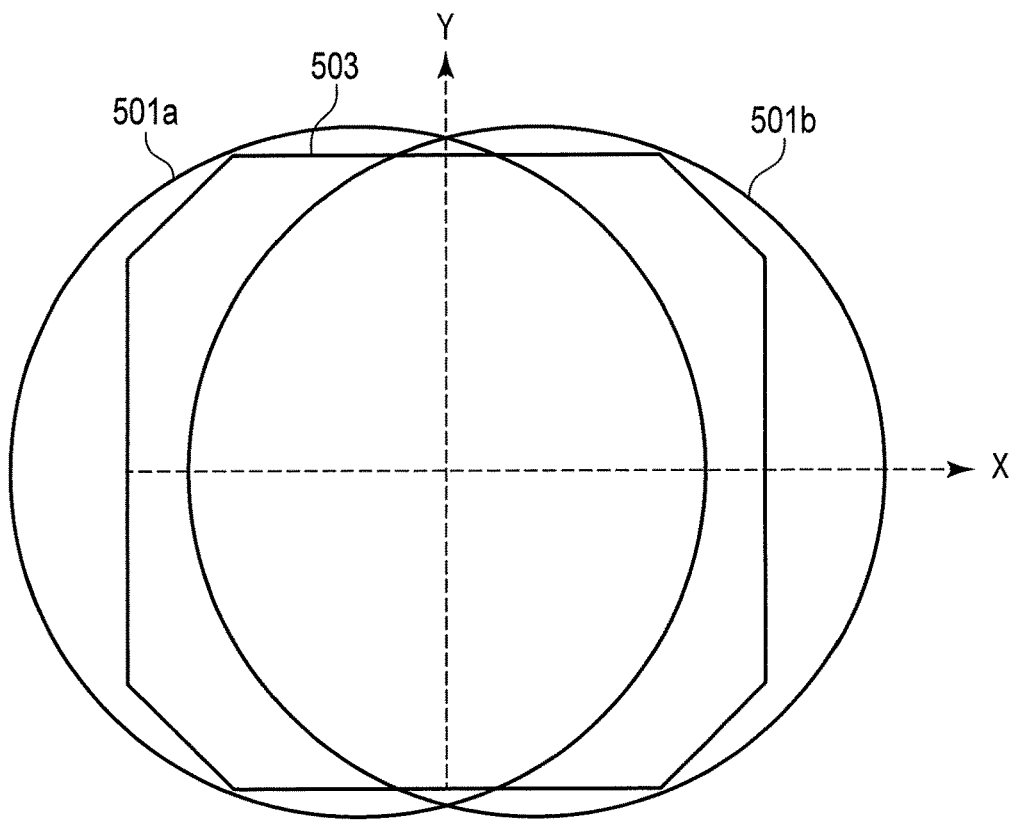
F I G. 4
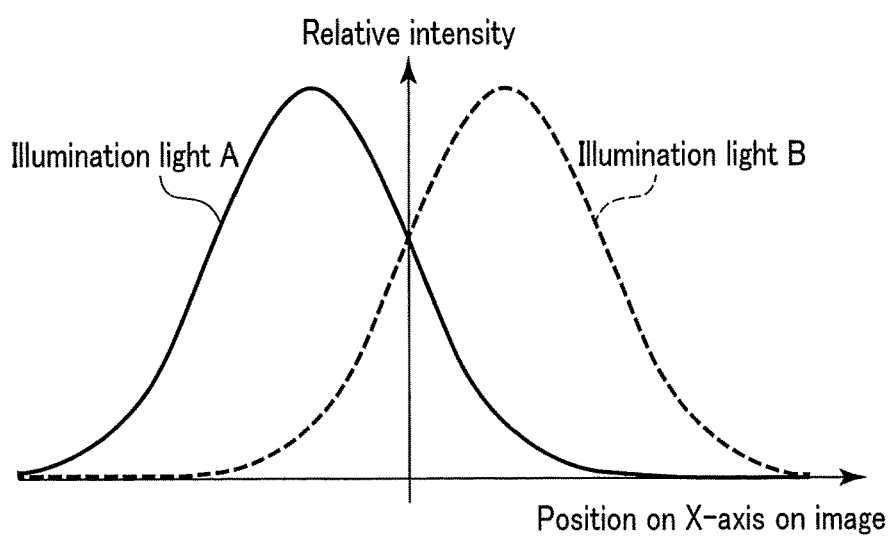
F I G. 5A

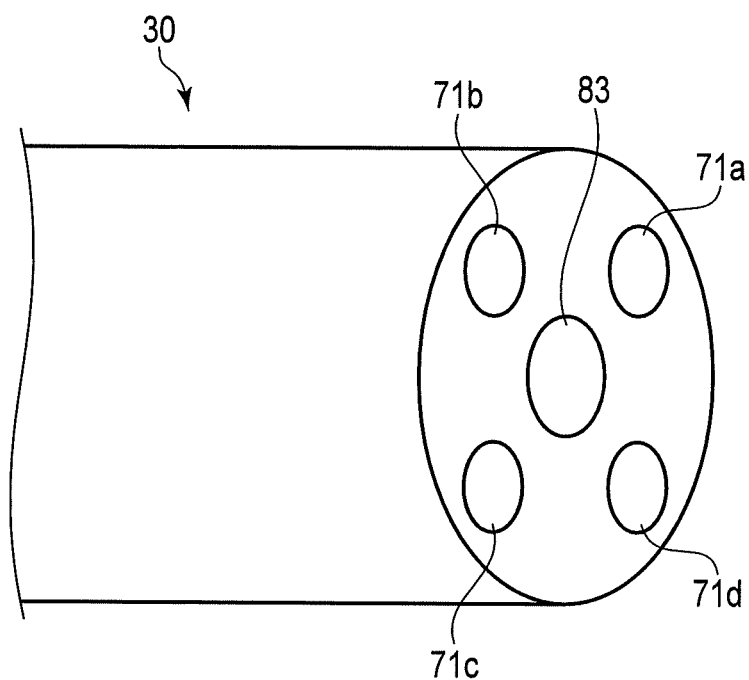
F I G. 15
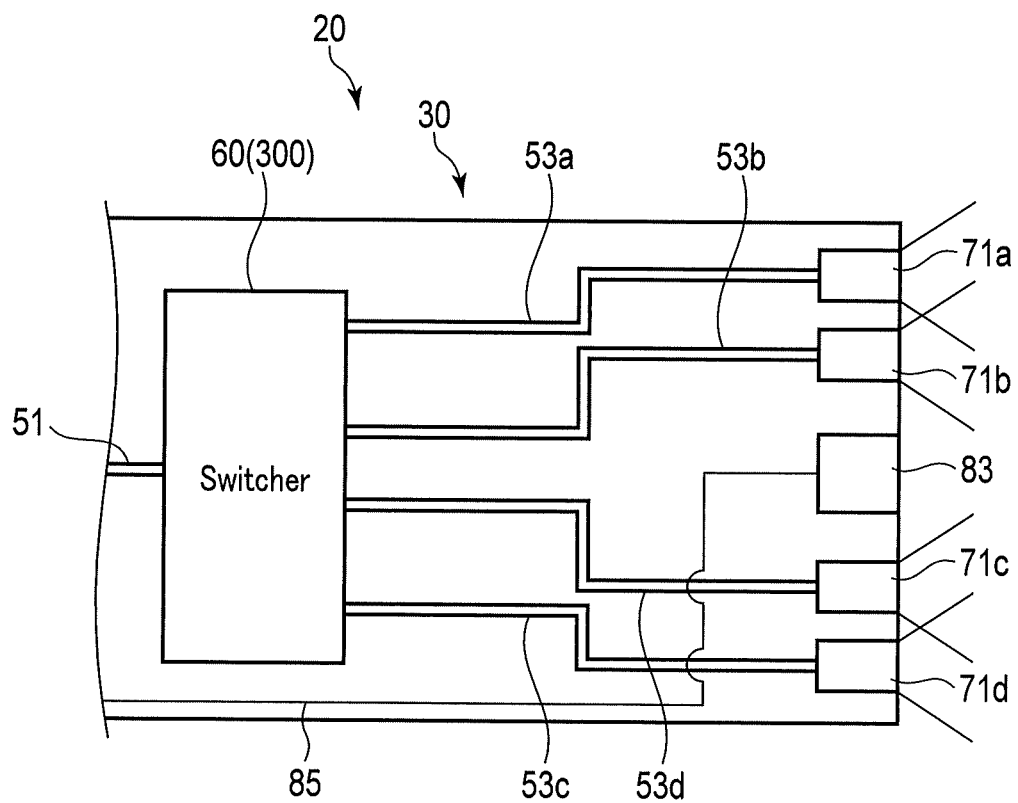
F I G. 16

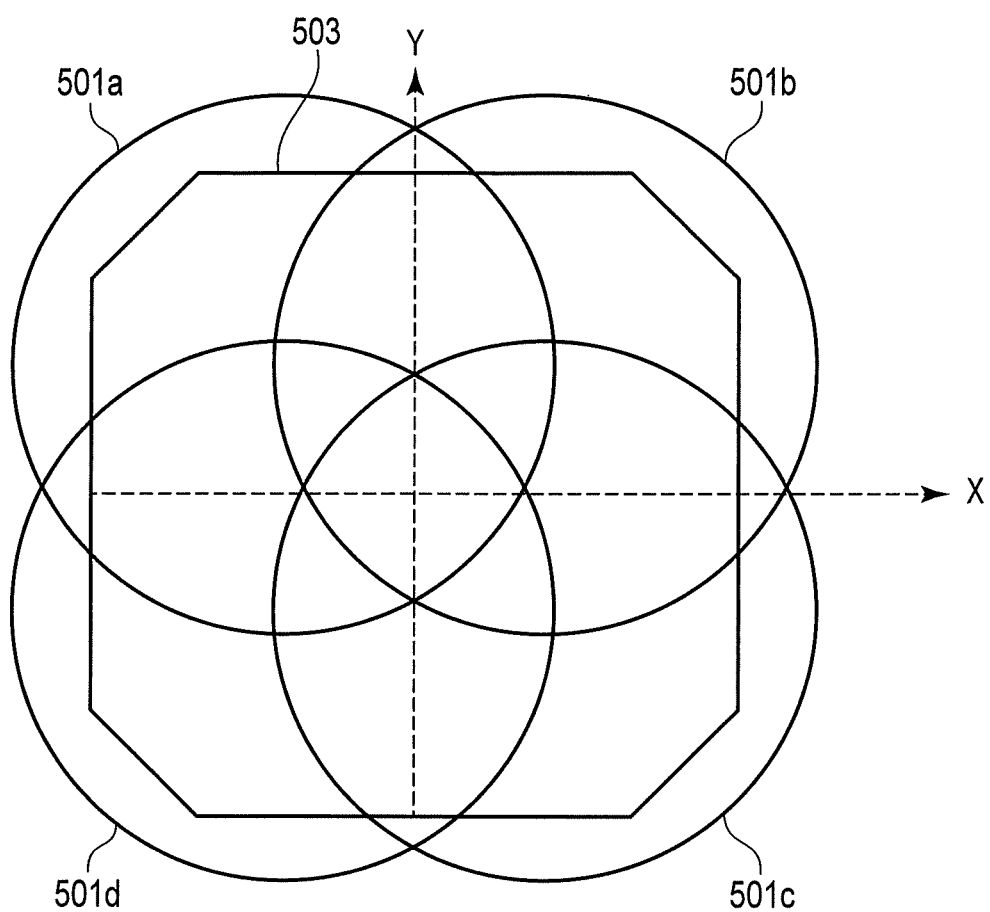
F I G. 17

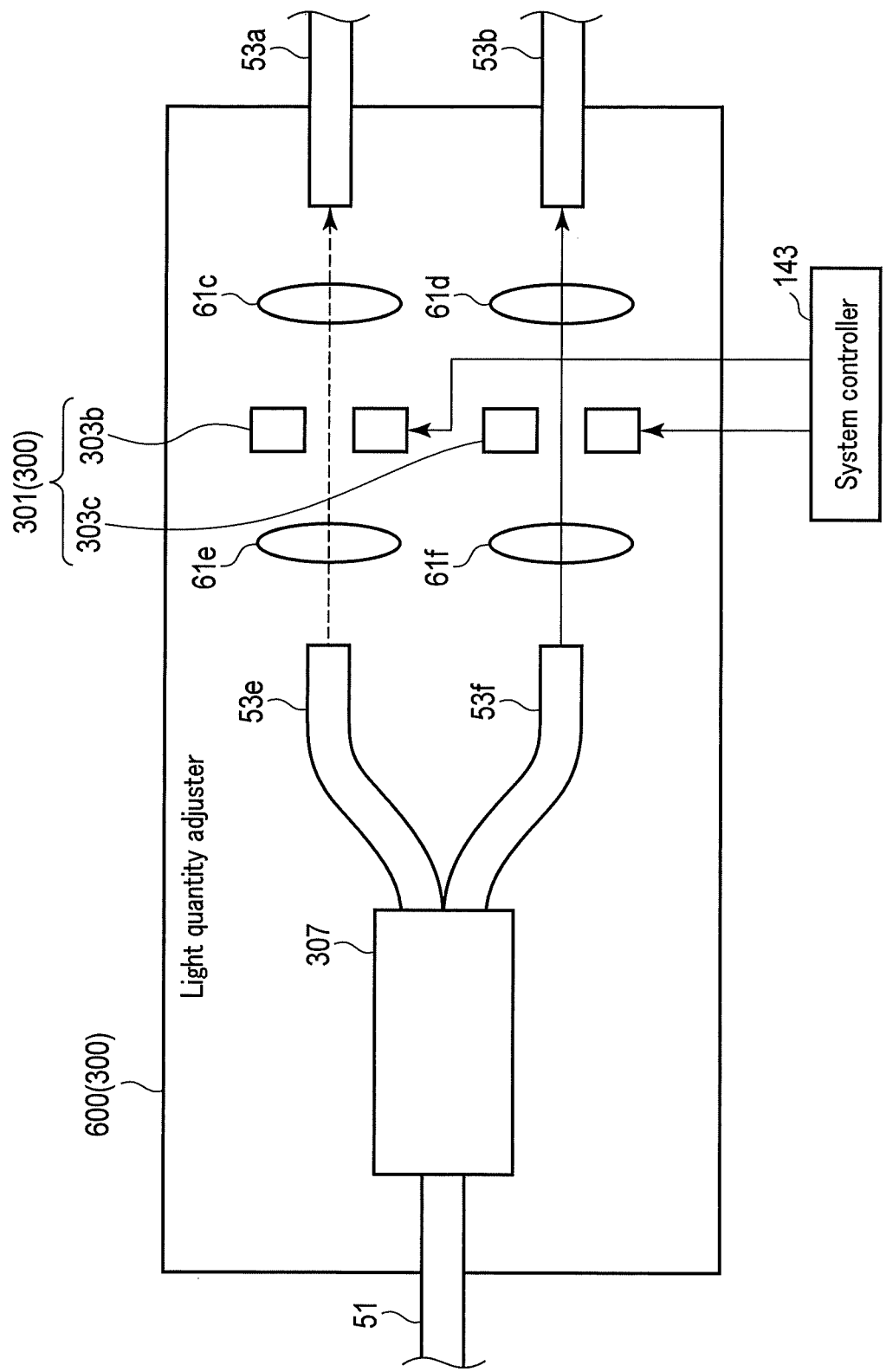
F I G. 24

ENDOSCOPE SYSTEM FOR ADJUSTING RATIO OF DISTRIBUTING PRIMARY LIGHT TO FIRST ILLUMINATOR AND SECOND ILLUMINATOR

CROSS-REFERENCE TO RELATED APPLICATIONS

This application is a Continuation Application of PCT Application No. PCT/JP2017/032702, filed Sep. 11, 2017, the entire contents of which are incorporated herein by reference.

BACKGROUND OF THE INVENTION

1. Field of the Invention

The present invention relates to an endoscope system.

2. Description of the Related Art

For example, an illumination device disclosed in Jpn. Pat. Appln. KOKAI Publication No. 2002-112959 is mounted on an endoscope system including an endoscope and a light source device connected to the endoscope. The illumination device includes first and second LED light sources disposed in the light source device, and first and second light guides that are disposed inside the endoscope and configured to guide illumination light emitted from the first and second LED light sources to a distal end of an insertion section of the endoscope, respectively. The illumination device further includes a light source controller that is disposed in the light source device and configured to independently control an emission light quantity of each of the first and second LED light sources in order to control each light quantity of the illumination light, and an imaging unit configured to perform imaging by use of reflection light reflected from an observation object.

Illumination light emitted from one of the first and second light guides illuminates a central portion of the observation object, and illumination light emitted from the other of the first and second light guides illuminates a peripheral portion disposed at a periphery of the central portion of the observation object. The imaging unit performs imaging by use of reflection light reflected from the observation object, and the light source controller controls the emission light quantity of each of the first and second LED light sources according to a light quantity of the reflection light captured by the imaging unit. Thereby, difference between luminance in the central portion and luminance in the peripheral portion is appropriately adjusted, and distribution of the illumination light for the observation object is appropriately adjusted.

BRIEF SUMMARY OF THE INVENTION

An endoscope system according to the present invention includes: a light source that is configured to emit primary light; plural illuminators that are configured to be irradiated with the primary light to emit plural respective illumination light generated based on the radiated primary light toward an observation object so that at least part of the plural illumination light overlap on the observation object; and an adjuster that is configured to desirably adjust a ratio of light quantities of the primary light that travels from the light source to the respective illuminators, so as to distribute the primary light to the respective illuminators.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram schematically showing an example of a configuration of an endoscope system according to a first embodiment of the present invention.

FIG. 2 is a diagram schematically showing an example of a configuration of a switcher in the endoscope system shown in FIG. 1.

FIG. 3 is an example of a timing chart showing relationships among operation timings of an imaging element that is a CMOS, a reflection member of the switcher, a light source, and two illuminators.

FIG. 4 is a diagram showing positional relationships between illuminated regions of two illumination light and an imaged region of an imaging element effective for a displayed image.

FIG. 5A is a diagram showing distributions of relative intensity of two illumination light on an observation object.

FIG. 15 is a perspective view showing an example of an arrangement configuration of the illuminators.

FIG. 16 is a diagram schematically showing the example of the arrangement configuration of the illuminators shown in FIG. 15.

FIG. 17 is a diagram showing positional relationships between illuminated regions of four illumination light emitted from the illuminators shown in FIG. 15 and an imaged region of the imaging element effective for a displayed image.

FIG. 24 is a diagram schematically showing an example of a configuration of an adjuster shown in FIG. 23.

DETAILED DESCRIPTION OF THE INVENTION

Figure 5B:
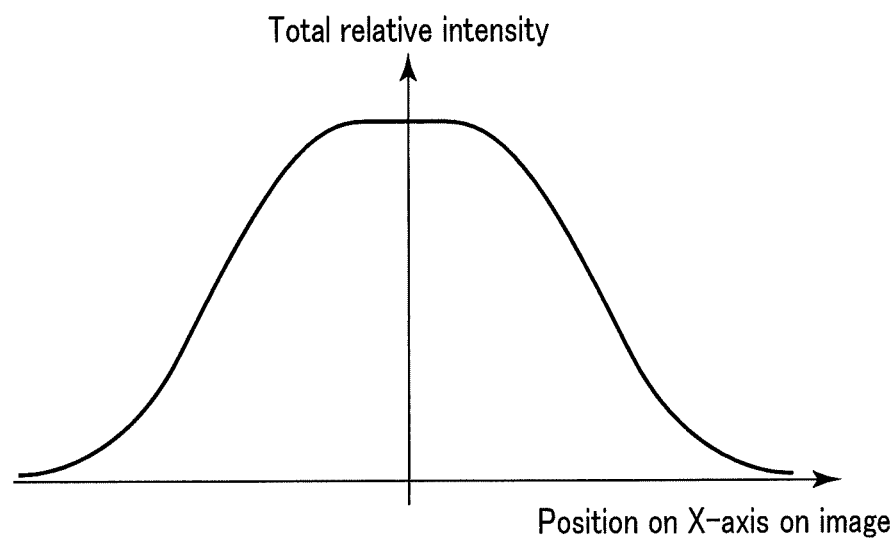
FIG. 5B is a diagram showing a distribution of total relative intensity obtained by totaling the distribution of relative intensity of one illumination light shown in FIG. 5A and the distribution of relative intensity of the other illumination light shown in FIG. 5A.

Hereinafter, each embodiment of the present invention will be described with reference to the drawings. Note that in some drawings, some members will be omitted and not shown for clarity of illustration.

First Embodiment

Hereinafter, a first embodiment of the present invention will be described.

As shown in FIG. 1, an endoscope system 10 includes an endoscope 20, a light source device 100 detachably connected to the endoscope 20, and a display device 200 connected to the light source device 100 and including, for example, a monitor. The endoscope 20 is inserted into, for example, a tube portion such as a lumen of a human body or the like, illuminates an observation object in the tube portion with illumination light, and images the observation object on the basis of reflection light from the observation object. This observation object is, for example, an affected part or a lesion in a body cavity. The display device 200 displays the imaged observation object as an image.

The endoscope 20 functions as, for example, an insertion apparatus to be inserted into a tube portion. The endoscope 20 may be a front-viewing endoscope 20 and may be a side-viewing endoscope 20. Although the endoscope 20 of the embodiment will be described as, for example, a medical endoscope 20, it is not necessary to be limited to this. The endoscope 20 may be an industrial endoscope 20 to be inserted into a tube portion of an industrial product such as a pipe.

The endoscope 20 is mentioned as an example of a small precision instrument, and an example of the precision instrument includes, for example, a catheter in addition to the endoscope 20.

The endoscope 20 includes a hollow elongated insertion section 30 to be inserted into, for example, a body cavity, and a control section 40 coupled to a proximal end of the insertion section 30 and configured to control the endoscope 20.

The insertion section 30 includes a distal hard section, a bendable section, and a flexible tube section in order from a distal end side of the insertion section 30 on the right side of a paper surface of FIG. 1 to a proximal end side of the insertion section 30 on the left side of the paper surface of FIG. 1. A proximal end of the distal hard section is coupled to a distal end of the bendable section, and a proximal end of the bendable section is coupled to a distal end of the flexible tube section. The flexible tube section is extended from the control section 40.

The control section 40 is grasped by an operator of the endoscope 20. The control section 40 includes an unshown bend control section configured to control bending of the bendable section, an unshown switch for air supply, water supply, suction, and imaging, and a universal cord 41 extended from a side of the control section 40. A connector 41a of the universal cord 41 is attachable to and detachable from the light source device 100.

The light source device 100 includes a light source 110 configured to emit primary light that is light source light for secondary light that is illumination light, and a first converging member 120.

The light source 110 includes plural light sources 111B, 111G, and 111R configured to emit primary light having wavelengths different from each other, and light guides 113B, 113G, and 113R that are optically connected to the light sources 111B, 111G, and 111R, and configured to guide the primary light emitted from the light sources 111B, 111G, and 111R, respectively. The light source 110 further includes a light coupler 115 optically connected to the light guides 113B, 113G, and 113R, and a light guide 117 optically connected to the light coupler 115.

The light source 111B includes, for example, a laser diode configured to emit blue laser light that is primary light. A central wavelength of the laser light is, for example, 445 nm.

The light source 111G includes, for example, a laser diode configured to emit green laser light that is primary light. A central wavelength of the laser light is, for example, 532 nm.

The light source 111R includes, for example, a laser diode configured to emit red laser light that is primary light. A central wavelength of the laser light is, for example, 635 nm.

In this way, the plural light sources 111B, 111G, and 111R emit plural primary light having wavelengths different from each other, respectively.

Note that the number of plural light sources, colors of light emitted from the plural light sources, and central wavelengths of the light are not specifically limited.

The light guides 113B, 113G, 113R, and 117 include, for example, optical fibers. The optical fibers may be, for example, single-core fibers.

The light guide 113B is optically connected to the light source 111B and light coupler 115, and guides the blue primary light emitted from the light source 111B to the light coupler 115. The light guide 113G is optically connected to the light source 111G and light coupler 115, and guides the green primary light emitted from the light source 111G to the light coupler 115. The light guide 113R is optically connected to the light source 111R and light coupler 115, and guides the red primary light emitted from the light source 111R to the light coupler 115.

In a traveling direction of the primary light from the light source 111B to the light coupler 115 and indicating from the left side to the right side of the paper surface of FIG. 1, an unshown second converging member may be disposed between the light source 111B and an entrance end of the light guide 113B. The second converging member includes a lens. The second converging member converges the primary light emitted from the light source 111B to the entrance end of the light guide 113B. In this way, the primary light emitted from the light source 111B only needs to be able to travel in order of the light guide 113B and light coupler 115. Here, although the description has been given using the light source 111B and light guide 113B, the second converging member may also be disposed between the light source 111G and light guide 113G and between the light source 111R and light guide 113R.

The light coupler 115 optically couples three primary light guided by the respective light guides 113B, 113G, and 113R as one light. When the wavelengths of the primary light are different from each other, and the primary light have the wavelengths of blue, green, and red as described above, light that has been optically coupled becomes, for example, white light. The light coupler 115 emits the white light that has been optically coupled toward the light guide 117 as primary light. The light coupler 115 functions as, for example, a light combiner or a spatial combining optical system.

The light guide 117 guides the primary light that is white light. The light guide 117 includes a light source side exit end 117a configured to emit the primary light toward the first converging member 120.

The first converging member 120 is disposed between the light source side exit end 117a and an endoscope side entrance end 51a described later in the traveling direction of the primary light. The first converging member 120 converges the primary light emitted from the light source side exit end 117a to the endoscope side entrance end 51a. The first converging member 120 includes, for example, a lens.

The endoscope 20 includes a light guide 51 having the endoscope side entrance end 51a, a switcher 60 optically connected to the light guide 51, two light guides 53a and 53b optically connected to the switcher 60, and illuminators 71a and 71b optically connected to the light guides 53a and 53b, respectively.

For example, the endoscope side entrance end 51a, light guide 51, and switcher 60 are disposed inside the connector 41a, the light guides 53a and 53b are disposed inside the connector 41a, inside the universal cord 41, inside the control section 40, and inside the insertion section 30, and the illuminators 71a and 71b are disposed inside the distal hard section, which is a distal end of the insertion section 30. It may be configured that the endoscope side entrance end 51a is disposed inside the connector 41a, the light guide 51 is disposed inside the connector 41a and inside the universal cord 41, and the switcher 60 is disposed inside the control section 40. The switcher 60 may be disposed at the distal end of the insertion section 30.

The primary light converged by the first converging member 120 enters the endoscope side entrance end 51a. The light guide 51 guides the primary light that has entered from the endoscope side entrance end 51a to the switcher 60.

In order to increase entrance efficiency of the primary light from the light source side exit end 117a to the endoscope side entrance end 51a, an unshown third converging member may be disposed. The third converging member is disposed, for example, inside the connector 41a, and disposed between the first converging member 120 and the endoscope side entrance end 51a in the traveling direction of the primary light. The third converging member converges the primary light converged to the third converging member by the first converging member 120 to the endoscope side entrance end 51a. The third converging member includes, for example, a lens.

The light guides 51, 53a, and 53b include, for example, optical fibers. The optical fibers may be, for example, single-core fibers. As the light guide 51, one fiber is disposed and optically connected to the light source 110. Therefore, in the embodiment, even if there are any number of illuminators 71a and 71b, one light source 110 and the light guide 51 that is one connection section optically connected to the one light source 110 are disposed. The light guides 53a and 53b are disposed in accordance with the number of the illuminators 71a and 71b.

The switcher 60 temporally switches the traveling direction of the primary light guided by the light guide 51 to any of the plural illuminators 71a and 71b. Specifically, the switcher 60 switches the traveling direction to either the light guide 53a optically connected to the illuminator 71a or the light guide 53b optically connected to the illuminator 71b. In the embodiment, although two illuminators 71a and 71b are disposed in the endoscope 20, it is not necessary to be limited to this, and the number of illuminators only needs to be plural as shown in FIGS. 15 and 16 described later. Consequently, the switcher 60 only needs to switch the traveling direction of the primary light to any one light guide of plural light guides optically connected to the respective illuminators.

A specific configuration of the switcher 60 will be described later.

When the traveling direction of the primary light is switched to the light guide 53a by the switcher 60, the light guide 53a guides the primary light guided by the light guide 51 to the illuminator 71a. When the traveling direction of the primary light is switched to the light guide 53b by the switcher 60, the light guide 53b guides the primary light guided by the light guide 51 to the illuminator 71b.

Since the configurations of the illuminators 71a and 71b are the same as each other, description will be made using the illuminator 71a here.

The illuminator 71a is irradiated with the primary light guided by the light guide 53a. The illuminator 71a converts at least part of the radiated primary light into illumination light. The illuminator 71a emits the illumination light to the observation object. The illuminator 71a like this includes, for example, an unshown diffusing member.

The diffusing member converts, without changing the wavelength of the primary light, at least part of the primary light radiated to the diffusing member into secondary light having the same wavelength as that of the primary light but having a light distribution angle different from that of the primary light. Then, the diffusing member emits the secondary light as white illumination light toward the outside, in particular, toward the observation object.

The diffusion here includes, for example, refraction, diffraction, and scattering, and the traveling direction of the diffused light changes to two or more directions by diffusion. Consequently, an illumination range of the illumination light emitted to the outside expands. The outside means forward, indicates a side opposite to the light guide 53a, and indicates the right side in FIG. 1.

For example, the diffusing member includes plural unshown diffusing particles and an unshown containing member that contains the diffusing particles.

The diffusing particles are distributed inside the containing member and sealed by the containing member. The diffusing particles are fine particles formed by, for example, a metal or a metal compound. Such diffusing particles are, for example, alumina, titanium oxide, and barium sulfate. Particle diameters of the diffusing particles are, for example, several hundred nm to several tens μm. A refractive index of the diffusing particles is different from that of the containing member. For example, the refractive index of the diffusing particles is preferably higher than that of the containing member. Thereby, the diffusing particles can improve light diffusivity.

The containing member is formed by a member that transmits the primary light and secondary light. Such a containing member is, for example, a transparent silicone resin or a transparent epoxy resin. The containing member has a high transmittance for the primary light and secondary light. The containing member seals a contained member. The containing member may be glass that seals the diffusing particles, which are alumina.

In the embodiment, the illuminator 71a only needs to be able to convert the primary light into illumination light having a desired light distribution or the like. Therefore, the illuminator 71a is not limited to the diffusing member, and may include another member, for example, a fluorescent member configured to emit fluorescence as illumination light. The diffusing member and fluorescent member function as a light converter configured to convert at least part of the primary light into illumination light that is secondary light having optical characteristics different from optical characteristics of the primary light. In addition, the illuminator 71a may emit only the second light as illumination light and may emit the primary light and secondary light as illumination light. Therefore, the illumination light includes at least the secondary light and may further include the primary light in addition to the secondary light.

The endoscope 20 includes a storage 81 disposed, for example, in the connector 41a. The storage 81 may be disposed in the control section 40. For example, the storage 81 may store a type of the endoscope 20 or optical characteristics of the endoscope 20 and imaging characteristics of an imager 83 described later. The optical characteristics of the endoscope 20 include, for example, light conversion characteristics of the illuminators 71a and 71b. For example, the storage 81 may store optical characteristics of plural illumination light in a later-described luminance adjustment region of the image and transmittance characteristics of later-described first and second traveling paths. The storage 81 stores a weighting factor that influences luminance of the image, for example, on the basis of any of the light conversion characteristics of the illuminators 71a and 71b, the imaging characteristics of the imager 83, and the transmittance characteristics of the first and second traveling paths. The storage 81 includes, for example, a ROM.

The endoscope 20 includes the imager 83 disposed inside the distal hard section, which is the distal end of the insertion section 30, and an imaging cable 85 disposed inside the endoscope 20.

The imager 83 is disposed between the illuminators 71a and 71b on a distal end plane of the distal hard section and is adjacent to the illuminators 71a and 71b. The imager 83 performs imaging by use of reflection light from the observation object illuminated with the illumination light. The imager 83 includes an unshown imaging element including, for example, a rolling shutter type CMOS, and an unshown lens configured to form an image on the imaging element from the reflection light reflected by the observation object.

The imaging cable 85 is electrically connected to the imager 83, and transmits an imaging result of the reflection light by the imager 83 as an electrical signal to the light source device 100.

The light source device 100 includes an image processor 130 configured to apply image processing to the signal transmitted from the imager 83 through the imaging cable 85 to generate an image by image processing. The image generated by the image processor 130 is output to the display device 200 and displayed on the display device 200. The image only needs to include at least one of a still image or a moving image.

The light source device 100 includes an input device 141 configured to allow an observation condition and the like to be input and set, and a system controller 143 configured to control the entire endoscope system 10. The light source device 100 further includes a light source controller 145 configured to independently control the light sources 111B, 111G, and 111R in order to control light quantities of the primary light emitted from the respective light sources 111B, 111G, and 111R, emission timings of the primary light, and emission times of the primary light, and a switching controller 147 configured to control switching of the switcher 60.

The input device 141 is, for example, a general input apparatus like a keyboard. The input device 141 may be, for example, a pointing device such as a mouse, a tag reader, a button switch, a slider, a dial, or a foot switch. The input device 141 may be used for the operator to input various commands to operate the endoscope system 10. The input device 141 as a button switch may be built in the control section 40.

For example, input information such as the observation condition input from the input device 141 and image information on the image from the image processor 130 are input into the system controller 143. For example, the system controller 143 accesses the storage 81 and reads storage information stored in the storage 81 when the connector 41a is connected to the light source device 100. The system controller 143 controls the light source 110 through the light source controller 145 and controls the switcher 60 through the switching controller 147 on the basis of at least one of the input information, image information, and storage information. The system controller 143 controls the light quantity of the primary light, the emission timing of the primary light, and the emission time of the primary light at the light source 110 through the light source controller 145, and controls the traveling direction, switching timing, and switching time of the primary light through the switching controller 147 and switcher 60. The system controller 143 may control the switcher 60 on the basis of the storage information stored in the storage 81.

For example, the light source controller 145 controls the light sources 111B, 111G, and 111R so that the light quantities of the primary light emitted from the respective light sources 111B, 111G, and 111R are substantially the same as each other and the light sources 111B, 111G, and 111R simultaneously emit the primary light for the same time.

The image processor 130, system controller 143, light source controller 145, and switching controller 147 are comprised of a hardware circuit including, for example, an ASIC. At least one of the image processor 130, system controller 143, light source controller 145, and switching controller 147 may be comprised of a processor. When at least one of them is comprised of a processor, an unshown internal memory or external memory accessible by the processor is disposed. The internal memory or external memory stores a program code for causing the processor to function as at least one of them when the processor executes the program code. In addition, the image processor 130, system controller 143, light source controller 145, and switching controller 147 may be formed by using one processor or may be formed by using plural processors. In the latter case, it is also possible to transmit and receive data to/from each other and process it in cooperation. In the latter case, it is also possible that they are disposed in respective housings of the light source device 100 different from each other.

When the image processor 130, system controller 143, light source controller 145, and switching controller 147 are comprised of a hardware circuit, they may be disposed in the control section 40.

Next, an example of a configuration of the switcher 60 will be described with reference to FIG. 2.

The switcher 60 includes first, second, third, and fourth lenses 61a, 61b, 61c, and 61d, a fixed reflection member 63a, and a movable reflection member 63b.

The first lens 61a converts the primary light guided by the light guide 51 into substantially parallel light or any convergent light.

The reflection member 63a reflects the substantially parallel light or any convergent light into which the first lens 61a has converted toward the reflection member 63b. The reflection member 63a includes, for example, a mirror.

The reflection member 63b switches the traveling direction of the primary light to the light guide 53a side or light guide 53b side. For this reason, the reflection member 63b is controlled by the switching controller 147 and switches the reflection direction of the primary light to the light guide 53a side or light guide 53b side by this control. In particular, by the control of the switching controller 147, the reflection member 63b can stop in a first state of reflecting the primary light toward the light guide 53a side or in a second state of reflecting the primary light toward the light guide 53b side. Here, the first and second states indicate, for example, an inclination of the reflection member 63b with respect to the central axis of the primary light emitted from an exit end of the light guide 51.

When the reflection member 63b stops in the first state, the reflection member 63b reflects the primary light toward the second lens 61b. The primary light is refracted at a first part of the second lens 61b and directed toward the third lens, and passes through the third lens 61c. As a result, the primary light that has passed through the second and third lenses 61b and 61c is converted into convergent light. The primary light travels to and enters the light guide 53a, is guided by the light guide 53a, and reaches the illuminator 71a.

When the reflection member 63b stops in the second state, the reflection member 63b reflects the primary light toward the second lens 61b. The primary light is refracted at a second part of the second lens 61b different from the first part and directed toward the fourth lens, and passes through the fourth lens 61d. As a result, the primary light that has passed through the second and fourth lenses 61b and 61d is converted into convergent light. The primary light travels to and enters the light guide 53b, is guided by the light guide 53b, and reaches the illuminator 71b.

In the embodiment, the reflection member 63b reflects all of the primary light radiated to the reflection member 63b, in other words, without leaking the primary light, toward the light guide 53a side or light guide 53b side.

The reflection member 63b includes a mirror manufactured by, for example, a micro electro mechanical systems (hereinafter referred to as MEMS) technique. Size of the reflection member 63b of the MEMS type has, for example, a side of several tens μm to several mm. The reflection member 63b of the MEMS type can switch the traveling direction of the primary light, for example, at a speed of 10 μs to several ms.

The second lens 61b is shared on the first and second traveling paths of the primary light in the endoscope system 10. The second lens 61b may be omitted. The first traveling path includes: the light source 110; the first converging member 120; the endoscope side entrance end 51a; the light guide 51; the first lens 61a, reflection member 63a, reflection member 63b, second lens 61b, and third lens 61c in the switcher 60; the light guide 53a; and the illuminator 71a. The second traveling path includes: the light source 110; the first converging member 120; the endoscope side entrance end 51a; the light guide 51; the first lens 61a, reflection member 63a, reflection member 63b, second lens 61b, and fourth lens 61d in the switcher 60; the light guide 53b; and the illuminator 71b.

The light guides 117 and 51 disposed on the traveling path of the primary light from the one light source 110 to the switcher 60 disposed in the connector 41a are shared by the first and second traveling paths from the light source 110 to the illuminators 71a and 71b. The light guide 51 optically connected to the light source 110 is optically connected to and shared by the illuminator 71a and light guide 53a on the first traveling path and the illuminator 71b and light guide 53b on the second traveling path.

The endoscope system 10 includes an adjuster 300 configured to desirably adjust a ratio of the light quantities of the primary light traveling to the respective illuminators 71a and 71b from the light source 110. The adjuster 300 distributes the primary light to the plural illuminators 71a and 71b at a desired ratio based on a target distribution of the illumination light on the observation object. In the embodiment, the adjuster 300 like this includes a light source controller 145 configured to desirably adjust the light quantity of the primary light, emission timing of the primary light, and emission time of the primary light at the light source 110, and the switcher 60 configured to desirably adjust the traveling direction of the primary light. Therefore, the adjuster 300 is disposed in the endoscope 20 and light source device 100.

Next, operation of the embodiment including the adjustment of the ratio will be described.

For convenience of description, the illumination light emitted from the illuminators 71a and 71b is referred to as illumination light A and B, respectively. Here, it is assumed that transmission efficiency of the primary light on the first traveling path when the primary light travels from the endoscope side entrance end 51a to the illuminator 71a is equal to transmission efficiency of the primary light on the second traveling path when the primary light travels from the endoscope side entrance end 51a to the illuminator 71b.

FIG. 3 is a timing chart showing relationships among operation timings of an imaging element of the imager 83, the reflection member 63b of the switcher 60, the light source 110, and the illuminators 71a and 71b when an image is captured in a state in which the light quantities of the illumination light A and B are the same as each other.

When the imaging element includes a CMOS or the like, generally, exposure timing of the imaging element and readout timing of the imaging element are different for each line of the imaging element. Consequently, there is a possibility that an image having different brightness is generated for each line depending on the readout timing and emission timings of the illumination light A and B at the illuminators 71a and 71b. Therefore, it is preferable that the illumination is performed within a time in which all the lines are in an exposure period.

In FIG. 3, a period during which all the lines are exposed is referred to as an exposure period, and a period during which any of the lines is reading out is referred to as a readout period. In the imaging element, the exposure period and readout period are repeatedly performed in this order, and an exposure period at a certain timing is referred to as an exposure period 1, 2, 3, . . . , and a readout period at a certain timing is referred to as a readout period 1, 2, 3, . . . . In FIG. 3, for simplification of illustration, only exposure periods 1, 2, and 3 and readout periods 1, 2, and 3 are shown. This simplification is also applied to FIGS. 8, 21, and 22.

The reflection member 63b switches to the first state at a timing when the exposure period 1 starts. In the exposure period 1, the reflection member 63b remains stationary in the first state. The reflection member 63b switches to the second state at a timing when the exposure period 1 ends. In the readout period 1, exposure period 2, and readout period 2, the reflection member 63b remains stationary in the second state. The reflection member 63b switches to the first state at a timing when the exposure period 3 starts. In the exposure period 3, the reflection member 63b remains stationary in the first state. The reflection member 63b switches to the second state at a timing when the exposure period 3 ends. In the readout period 3, the reflection member 63b remains stationary in the second state. The reflection member 63b performs such switching, controlled by the system controller 143 through the switching controller 147.

The light source 110 emits primary light having a desired light quantity in the exposure periods 1, 2, 3, . . . . In particular, the primary light is simultaneously emitted by the light sources 111B, 111G, and 111R of the light source 110 and the light quantities of the primary light are the same as each other. The light sources 111B, 111G, and 111R stop in the readout periods 1, 2, 3, . . . , and do not emit the primary light. The light sources 111B, 111G, and 111R perform such driving, controlled by the system controller 143 through the light source controller 145.

In a state in which the light source 110 is emitting the primary light in a state in which the reflection member 63b has stopped in the first state, that is, in the exposure periods 1 and 3, the illuminator 71a emits the illumination light A and the illuminator 71b does not emit the illumination light B. In a state in which the light source 110 is emitting the primary light in a state in which the reflection member 63b has stopped in the second state, that is, in the exposure period 2, the illuminator 71a does not emit the illumination light A and the illuminator 71b emits the illumination light B. In any of the readout periods 1, 2, 3, . . . , since the light source 110 stops and the primary light is not emitted, the illuminator 71a and 71b do not emit the illumination light A and B. In this way, the switching, emission, and stop of the primary light, and exposure are synchronized with each other.

The imaging element transmits reflection light from the observation object obtained in each of the exposure periods 1, 2, 3, . . . as an electric signal to the image processor 130 through the imaging cable 85. The image processor 130 applies image processing to the electric signal to generate image information 1, 2, 3, . . . . The image processor 130 combines two by two from the image information 1, 2, 3, . . . , for example, combines the image information 1 and image information 2, and combines the image information 3 and image information 4, to generate an image. That is, the image processor 130 combines images obtained at plural respective imaging frames within a cycle in which plural imaging frames of the imager 83 are set as one cycle to generate an image. The image processor 130 performs correction such as enhancement processing and color correction processing on the composite image. Then, the display device 200 displays the corrected image.

Here, FIG. 4 is a diagram showing positional relationships between illuminated regions 501a and 501b of the illumination light A and B on a region of the observation object away by a certain distance from the illuminators 71a and 71b and an imaged region 503 of the imaging element effective for a displayed image. The illuminators 71a and 71b are disposed at different positions on the distal end plane of the distal hard section. Consequently, when the illuminators 71a and 71b emit the illumination light A and B to the observation object, respectively, the centers of the illuminated regions 501a and 501b in the imaged region 503 are shifted from each other.

In the embodiment, the image is assumed to include a luminance adjustment region that is a region where luminance can be adjusted in the imaged region 503 of the imaging element effective for the displayed image. As described above, when the observation object is illuminated with the illumination light A and B, each of the illuminated regions 501a and 501b of the respective illumination light A and B is disposed on the observation object. The centers of the illuminated regions of the two illumination light A and B are supposed to be disposed at positions different from each other on the observation object corresponding to the luminance adjustment region of the image.

Generally, the intensity of the illumination light A and B is high at the centers of the illuminated regions 501a and 501b and gradually decreases from the centers toward the outer peripheral edges of the illuminated regions 501a and 501b. FIG. 5A shows distributions of relative intensity of the illumination light A and B on the observation object assumed to be a plane. FIG. 5B shows a distribution of total relative intensity obtained by totaling the distribution of relative intensity of the illumination light A shown in FIG. 5A and the distribution of relative intensity of the illumination light B shown in FIG. 5A.

Here, distance between the distal end plane of the distal hard section where the illuminators 71a and 71b are disposed and the observation object assumed to be a plane is defined as first distance. Supposedly, the first distance is always constant while the endoscope 20 is executing observation operation and observation objects in the illuminated regions 501a and 501b are the same material. In this case, the endoscope system 10 can always obtain an image having the luminance distribution shown in FIG. 5B.

Figure 6:
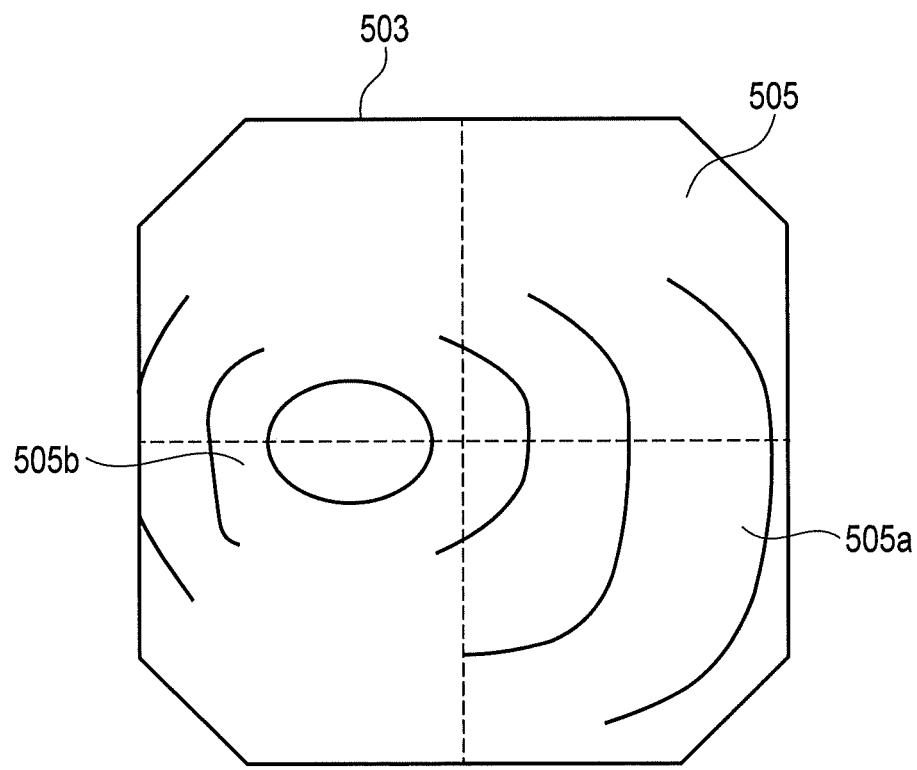
FIG. 6 shows an image when an insertion section is inserted into an intestine tract.

However, assuming actual observation operation of the endoscope 20, the insertion section 30 is inserted into a tube portion such as a stomach or an intestine tract, and it is sufficiently conceivable that the observation object is uneven and not a flat surface, such as a stomach wall or an intestine wall. Then, an angle of the observation target with respect to the distal end plane changes dynamically, and the first distance changes for each observation object. For example, in a state in which the distributions of relative intensity of the illumination light A and B shown in FIG. 5A are obtained, when the insertion section 30 is inserted into an intestine tract 505 as shown in FIG. 6, a light quantity of reflection light reflected from an intestine wall 505a near the distal end plane becomes larger than a light quantity of reflection light reflected from an intestine wall 505b far from the distal end plane. Here, the near intestine wall 505a indicates a region in a withdrawal direction of the insertion section 30 with respect to the intestine tract, and refers to a near side of the intestine tract 505. The far intestine wall 505b indicates a region in an insertion direction of the insertion section 30 with respect to the intestine tract 505, and refers to a deep side of the intestine tract 505 opposite to the near side of the intestine tract 505. Then, on the image, since luminance is high at the near intestine wall 505a, the near intestine wall 505a is displayed bright, and since luminance is low at the far intestine wall 505b, the far intestine wall 505b is displayed dark. As a result, the bias of luminance distribution as shown in FIG. 7 occurs on the image in the luminance adjustment region of the image.

In the embodiment, for example, before the insertion section 30 is inserted into an intestine tract, luminance of an image serving as a target suitable for observation is set in a desired certain range within the luminance adjustment region of the image. This set range is referred to as a target luminance region. The setting of the target luminance region may be implemented on the basis of luminance of a past image captured when the insertion section 30 has been inserted into an intestine tract in the past. For example, this setting may be set manually through the input device 141 by the operator of the endoscope 20 who is viewing the display device 200 that displays a past image stored in the unshown storage of the light source device 100 and may be set by the system controller 143 on the basis of the past image stored in the unshown storage. A region other than the target luminance region within the luminance adjustment region of the image is referred to as an outside region. When the bias of the luminance distribution as shown in FIG. 7 occurs on the image, the image includes the target luminance region and the outside region having luminance outside the desired target luminance region in the luminance adjustment region. If the luminance of the outside region is higher than the luminance of the target luminance region, the image will be overexposed, and if the luminance of the outside region is lower, the image will be blackened. Then, in the image, a depth range for observation is reduced.

Therefore, in the embodiment, in order to eliminate reduction in the depth range, the system controller 143 needs to adjust (improve) the luminance distribution so that the luminance distribution in the luminance adjustment region approaches the target luminance distribution of the illumination light on the observation object. Here, the target luminance distribution is an example of the target distribution of the illumination light on the observation object serving as a base of the desired ratio adjusted by the adjuster 300. In addition, approaching the target luminance distribution indicates that the entire luminance distribution in the luminance adjustment region falls within the target luminance region. Therefore, the system controller 143 adjusts (improves) the luminance distribution so that the luminance of the outside region falls within the target luminance region. In order to adjust the luminance distribution, the system controller 143 controls a ratio of the light quantities of the primary light traveling to the respective illuminators 71a and 71b through the light source controller 145 and switcher 60, which serve as the adjuster 300.

Figure 7:
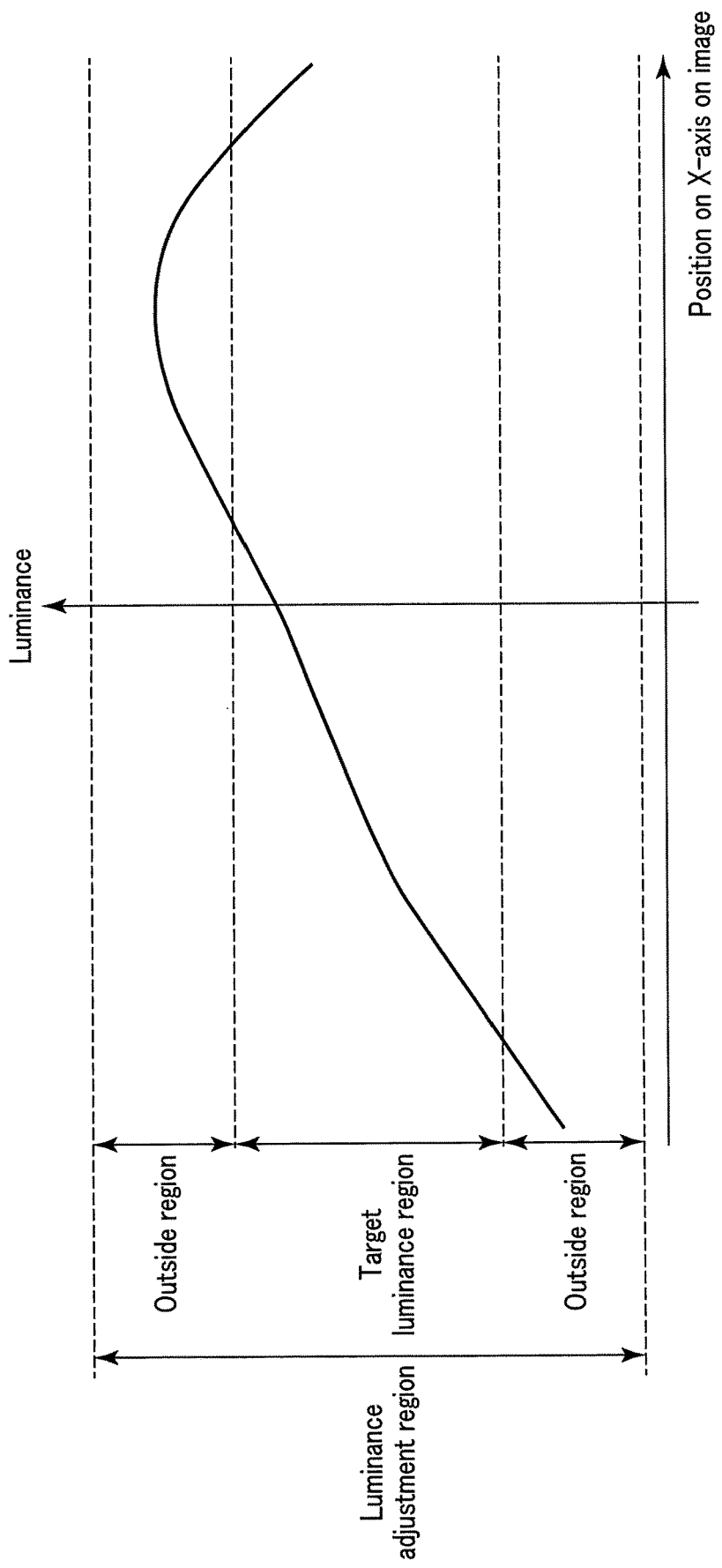
FIG. 7 is a diagram showing that bias of a luminance distribution has occurred within a luminance adjustment region of the image.
Figure 8:
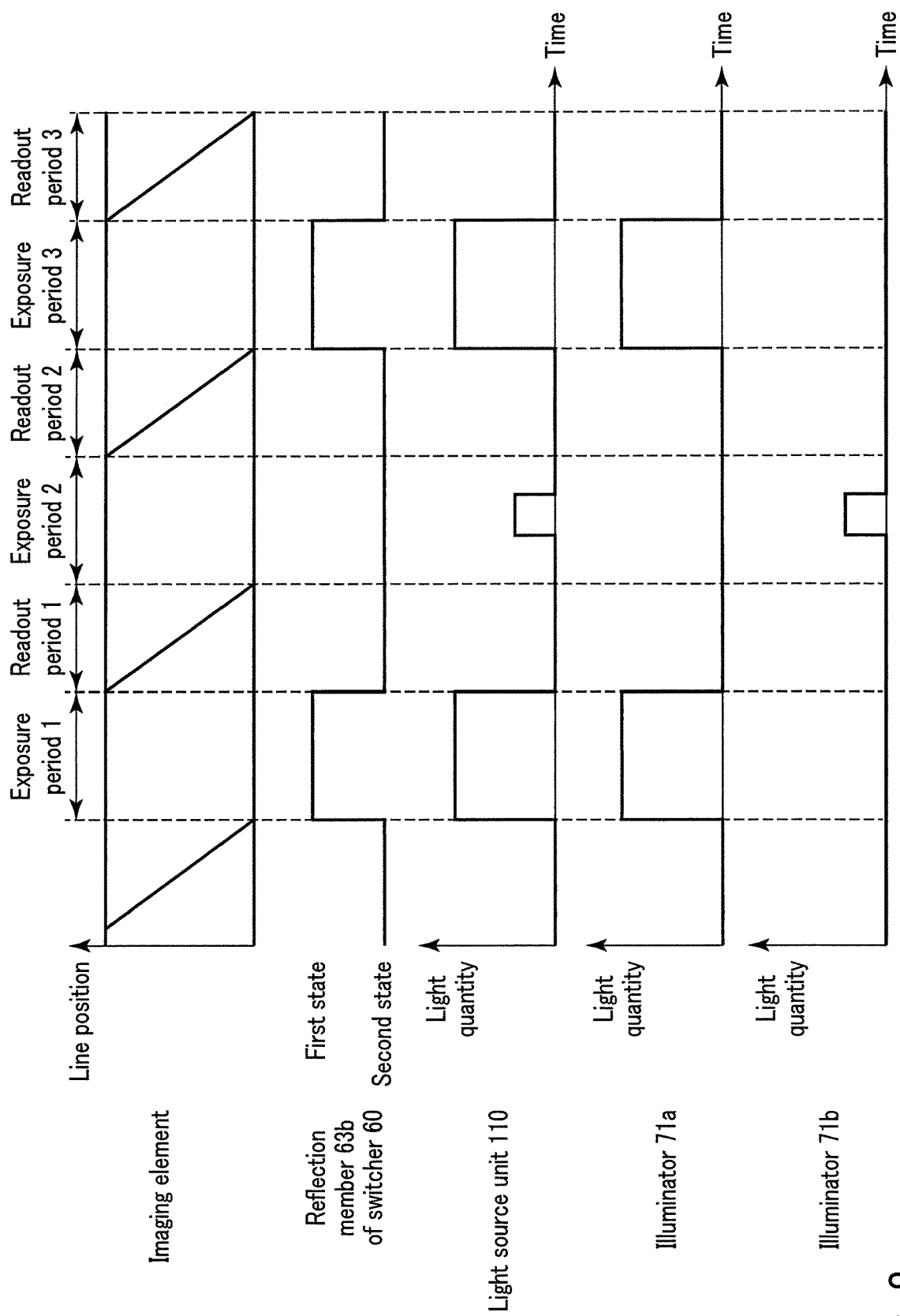
FIG. 8 is an example of a timing chart in which a light quantity and an illumination time of illumination light of one illuminator are changed in the timing chart shown in FIG. 3 in order to adjust the luminance distribution shown in FIG. 7.

FIG. 8 is a timing chart in which the light quantity and illumination time of the illumination light B of the illuminator 71b are changed in the timing chart shown in FIG. 3 in order to adjust the luminance distribution shown in FIG. 7. In FIG. 8, switching of the reflection member 63b is the same as that in FIG. 3.

When FIG. 8 is compared with FIG. 3, the system controller 143 controls the light source controller 145 in the exposure periods 1 and 3 to adjust the luminance distribution, and by this control, the light quantity of the primary light emitted from the light source 110 increases and the light quantity of the illumination light A of the illuminator 71a increases. Thereby, brightness in the exposure periods 1 and 3 increases. In order to adjust the luminance distribution, the system controller 143 controls the light source controller 145 in the exposure period 2, and by this control, a light emission time (operation time) of the light source 110, which is an emission time of the primary light, shortens. In addition, the light quantity of the primary light emitted from the light source 110 decreases and the light quantity of the illumination light B of the illuminator 71b decreases. Thereby, brightness in the exposure period 2 decreases. Here, the brightness means a multiplication value of the illumination time of the illumination light A or B, which is the emission time of the primary light at the light source 110, by the light quantity of the illumination light A or B, which is the light quantity of the primary light at the light source 110. In FIG. 8, the multiplication value is adjusted by adjustment of both illumination time and light quantity, and the luminance distribution is adjusted by the adjustment of the multiplication value. Note that the multiplication value, in other words, the luminance distribution only needs to be adjusted by at least one of the illumination time and light quantity.

As shown in FIG. 8, the adjuster 300, which includes the switcher 60, distributes a multiplication light quantity per unit time relating to imaging processing of the imager 83 to each of the plural illuminators 71a and 71b. The multiplication light quantity means the above-described brightness, that is, the multiplication value of the illumination time of one illumination light by the light quantity of the one illumination light, and the multiplication value of the emission time of the primary light at the light source 110 by the light quantity of the primary light at the light source 110. The system controller 143 adjusts a switching time of the switcher 60 and adjusts a multiplication light quantity ratio within the unit time by the adjustment of the switching time within the unit time. The multiplication light quantity ratio is a ratio between the multiplication light quantity of the illumination light A and the multiplication light quantity of the illumination light B. The adjuster 300, which includes the light source controller 145, adjusts the light quantity of the primary light emitted from the light source 110 and can desirably adjust the light quantity of the primary light radiated to the illuminators 71a and 71b by this adjustment. The system controller 143 adjusts combination of the radiation time of the primary light radiated to the illuminators 71a and 71b and the light quantity of the primary light radiated to the illuminators 71a and 71b through the adjuster 300, which is the light source controller 145. The system controller 143 adjusts the multiplication light quantity ratio by adjusting the combination. The light source controller 145 controls the light source 110 in order to adjust the light quantity of the primary light emitted from the light source 110. The system controller 143 adjusts the light quantity of the primary light radiated to the illuminators 71a and 71b by adjusting the light quantity of the primary light at the light source 110 in synchronization with switching of the switcher 60 through the light source controller 145. The adjuster 300, which is the light source controller 145, adjusts the multiplication light quantity ratio within the unit time within the exposure period of the imager 83 to a desired value in a cycle in which plural imaging frames of the imager 83 are set as one cycle.

Figure 9A:
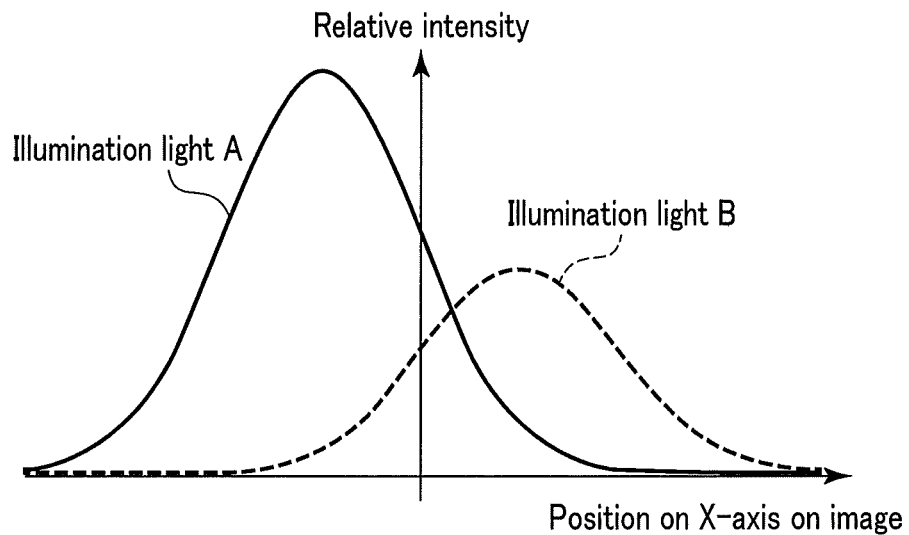
FIG. 9A is a diagram showing distributions of relative intensity of the two illumination light on the observation object when the observation object is illuminated with the two illumination light at a light quantity ratio indicated in FIG. 8.
Figure 9B:
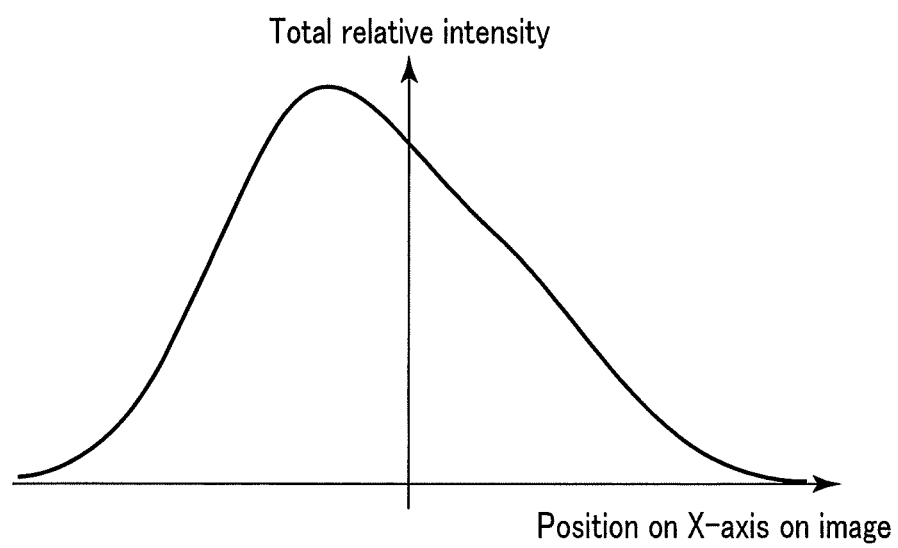
FIG. 9B is a diagram showing a distribution of total relative intensity obtained by totaling the distribution of relative intensity of one illumination light shown in FIG. 9A and the distribution of relative intensity of the other illumination light shown in FIG. 9A.

FIG. 9A shows distributions of relative intensity of the illumination light A and B on an observation object when the observation object assumed to be a plane is illuminated with the illumination light A and B at the light quantity ratio indicated in FIG. 8. FIG. 9B shows a distribution of total relative intensity obtained by totaling the distribution of relative intensity of the illumination light A shown in FIG. 9A and the distribution of relative intensity of the illumination light B shown in FIG. 9A. When FIGS. 9A and 9B are compared with FIGS. 5A and 5B, the distribution of the total relative intensity is biased toward the illumination light A side due to the decrease in the illumination time and light quantity of the illumination light B.

Figure 10:
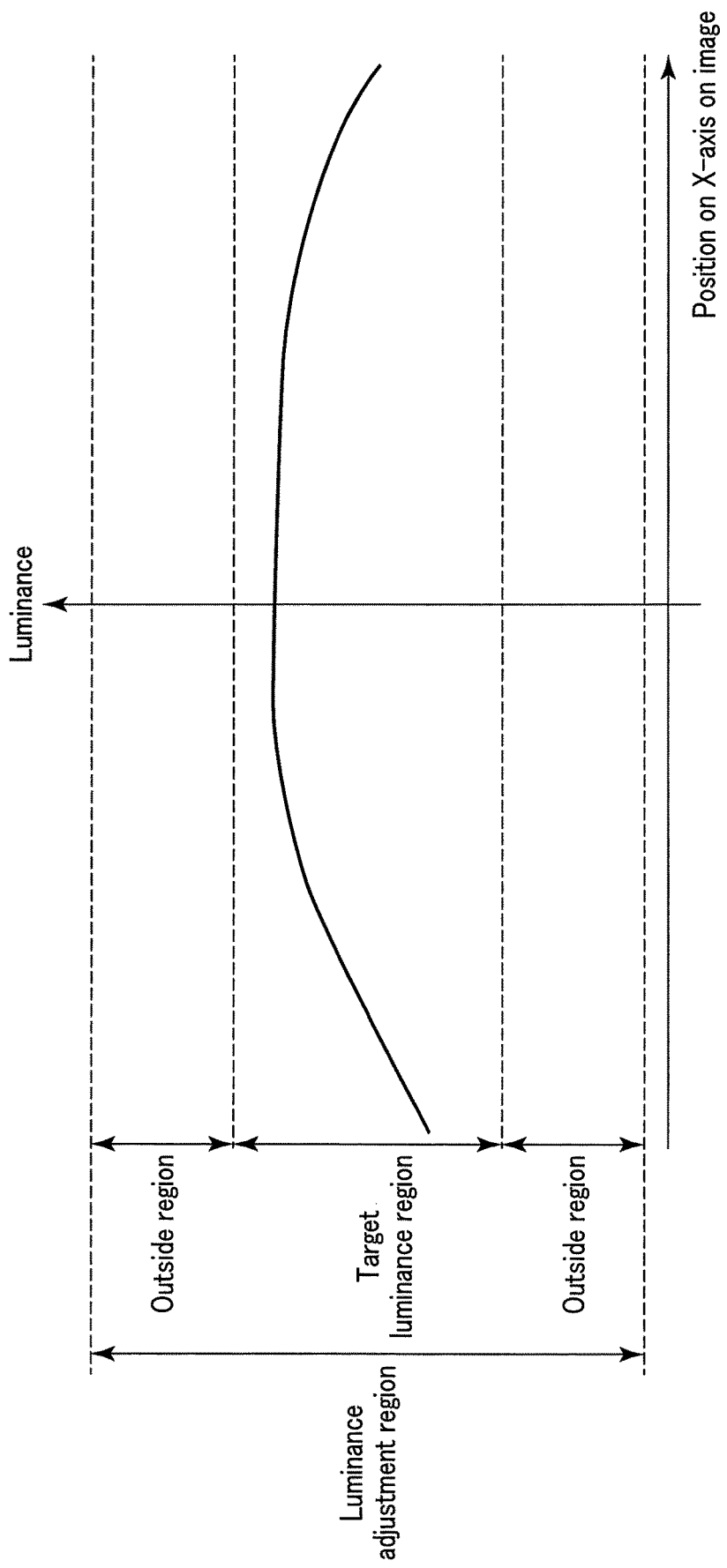
FIG. 10 is a diagram showing that the bias of the luminance distribution is eliminated in the luminance adjustment region of the image, and that the luminance distribution is substantially uniformed and falls within a target luminance region.

However, as shown in FIG. 10, the luminance of the outside region shown in FIG. 7 falls within the target luminance region, and the luminance distribution in the luminance adjustment region is substantially uniformed over the entire image and falls within the target luminance region. Consequently, the image is prevented from being overexposed and from being blackened, and the depth range for observation on the image is prevented from being reduced.

The system controller 143 preferably performs feedback control of the light quantity ratio so that most of the luminance distribution in the luminance adjustment region falls within the target luminance region. For example, the system controller 143 may control the light quantity ratio to a direction in which the luminance distribution becomes constant through the adjuster 300, which is the light source controller 145, on the basis of the weighting factor stored in the storage 81. The direction in which the luminance distribution becomes constant means that, for example, the luminance distribution in the luminance adjustment region is substantially uniformed over the entire image and falls within the target luminance region. Alternately, the system controller 143 changes the light quantity ratio in a certain direction by using, for example, hill-climbing control. For example, the system controller 143 gradually increases the light quantity of one illumination light among the plural illumination light through the adjuster 300. If area of the outside region increases or the maximum luminance in the outside region increases by the increase, then the system controller 143 gradually decreases the light quantity through the adjuster 300.

Figure 11:
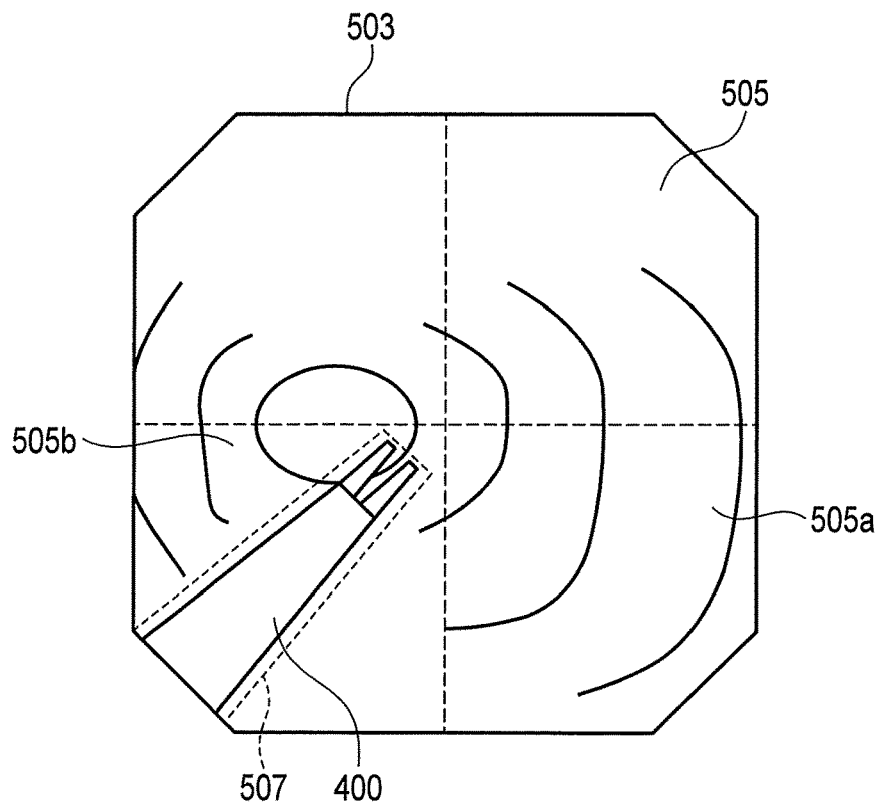
FIG. 11 is a diagram illustrating an adjustment exclusion region.

When a treatment tool 400 (see FIG. 11) such as forceps is used while the endoscope 20 is executing observation operation, the treatment tool 400 appears in an image. Therefore, the system controller 143 may remove an image region where the treatment tool 400 is displayed from luminance calculation. Generally, the treatment tool 400 has a metal color and is linear. The image of the metallic treatment tool 400 has a singularly high luminance. The system controller 143 recognizes a region where one of a subject having a metal color (for example, the treatment tool 400) and an artifact (for example, the treatment tool 400) having a linear shape appears within the luminance adjustment region of the captured image as an adjustment excluding region 507 that is a region where the treatment tool 400 appears. The adjustment excluding region 507 may include regions around the subject and artifact. The system controller 143 then sets the adjustment excluding region 507 within the luminance adjustment region. The system controller 143 excludes the adjustment excluding region 507 from the captured image and sets a region after exclusion as the target luminance region and outside region. In this way, when the system controller 143 excludes a region having a singularly high luminance from the captured image, it is possible to increase the depth range for observation.

In the embodiment, the one light source 110 is only used and it is not necessary to add light sources other than the one light sources 110 according to an observation object or a use of the endoscope 20. Regardless of the number of illuminators 71*a* and 71*b*, one light source 110 and the light source controller 145 and switcher 60 serving as the adjuster 300 distribute the light quantity of the primary light to each of the plural illuminators 71*a* and 71*b* from the one light source 110 at the desired ratio based on the target luminance distribution, which is a target distribution of the illumination light on the observation object. The switcher 60 only needs to switch the traveling direction of the primary light to any one light guide of the plural light guides optically connected to the respective illuminators.

Thereby, in the embodiment, it is possible to provide the endoscope system 10 capable of adjusting the distribution of illumination light by using only the one light source 110. In the embodiment, since the one light source 110 is only needed, the endoscope system 10 can be reduced in cost. In the embodiment, the illuminators 71*a* and 71*b* can be disposed according to a use by switching of the switcher 60, and the endoscope system 10 can have scalability.

In the embodiment, whatever the observation target and the type of the endoscope 20 are, the luminance of the outside region can be fallen within the target luminance region, and the luminance distribution in the luminance adjustment region can be substantially uniformed over the entire image and can be fallen within the target luminance region. As a result, it is possible to prevent the depth range for observation from being reduced in the image.

The switcher 60, which is the adjuster 300, distributes the multiplication light quantity per unit time relating to the imaging processing of the imager 83 to each of the plural illuminators 71*a* and 71*b*. Accordingly, the light quantity ratio during the exposure period can be adjusted, and the luminance distribution in the luminance adjustment region can be substantially uniformed over the entire image and can be fallen within the target luminance region, and scalability can be increased.

The system controller 143 controls the ratio through the adjuster 300 (light source controller 145 and switcher 60) so that the luminance distribution of the luminance adjustment region approaches the target luminance distribution, which is a target distribution. In particular, the system controller 143 controls the ratio through the adjuster 300 so that the luminance in the outside region falls within the target luminance region. Thereby, it is possible to prevent the depth range for observation from being reduced on the image, and optimal observation can be provided.

For example, if the area of the outside region is increased or the maximum luminance in the outside region is increased by the increase of the light quantity of the illumination light A, the system controller 143 reduces the light quantity of the illumination light A through the light source controller 145, which is the adjuster 300. By such hill-climbing control, the luminance distribution in the luminance adjustment region can always be fallen within the target luminance region.

The system controller 143 controls the light quantity ratio through the light source controller 145, which is the adjuster 300, on the basis of the weighting factor. As a result, the luminance distribution in the luminance adjustment region can always be fallen within the target luminance region.

The system controller 143 sets the region excluding the adjustment excluding region 507 from the image as the target luminance region and outside region. Consequently, it is possible to exclude a region having a singularly high luminance from the captured image, increase the depth range for observation, and increase scalability.

The system controller 143 adjusts the switching time of the switcher 60, and adjusts the multiplication light quantity ratio within the unit time by adjusting the switching time within the unit time. The system controller 143 adjusts the combination of the illumination time of the primary light and the light quantity of the primary light through the light source controller 145, which is the adjuster 300, and thereby adjusts the multiplication light quantity ratio. The system controller 143 adjusts the light quantity of the primary light at the light source 110 in synchronization with switching of the switcher 60 through the light source controller 145. Then, the system controller 143 adjusts the light quantity of the primary light radiated to the illuminators 71a and 71b. Therefore, the light quantity ratio during the exposure period can be adjusted.

The system controller 143 controls the switcher 60 on the basis of the storage information stored in the storage 81. Consequently, for observation of various types of endoscopes 20 connected to the light source device 100, the luminance of the outside region can be fallen within the target luminance region and the luminance distribution in the luminance adjustment region can be substantially uniformed over the entire image and can be fallen within the target luminance region.

In the embodiment, one light source 110 and the light guide 51 of the endoscope 20, which is one connection section optically connected to the one light source 110, are disposed. Consequently, each of the light guides 53a and 53b does not need to be directly and optically connected to the light source 110 and the endoscope system 10 can be simplified in the configuration and reduced in cost.

The above-described configuration of the embodiment is an example and the configuration of the embodiment does not need to be limited to this.

For example, the light source 110 is not limited to a laser diode and may include a Xe lamp, an LED, or the like. An emission point of primary light of the Xe lamp or the like is larger than the emission point of primary light of the laser diode. Consequently, a light guide configured to guide the primary light emitted from the Xe lamp or the like to the first converging member 120 is not limited to a single-core optical fiber and may include a bundle fiber.

For example, the arrangement of the light guides 113B, 113G, 113R, 117, 51, 53a, and 53b does not need to be limited to the above description. In the embodiment, the light guides, which are single-core optical fibers, only need to be disposed according to the arrangement of the one light source 110 and the plural illuminators 71a and 71b. Therefore, the light guides only need to be disposed on the traveling path of the primary light that travels from the light source 110 to the plural illuminators 71a and 71b, and be able to guide the primary light from the light source 110 to the plural illuminators 71a and 71b. The switcher 60, which is the adjuster 300, only needs to be disposed on the traveling path. Between the one light source 110 and adjuster 300, at least one light guide only needs to be disposed. When plural light guides are disposed, the light guides only need to be optically connected to each other. One or more light guides disposed between the one light source 110 and adjuster 300 only need to be shared by plural traveling paths between the adjuster 300 and plural illuminators. In addition, in the readout period, the reflection member 63b is in the first state but it may be in the second state.

The configuration of the switcher 60 is not limited to the configuration shown in FIG. 2.

Figure 12:
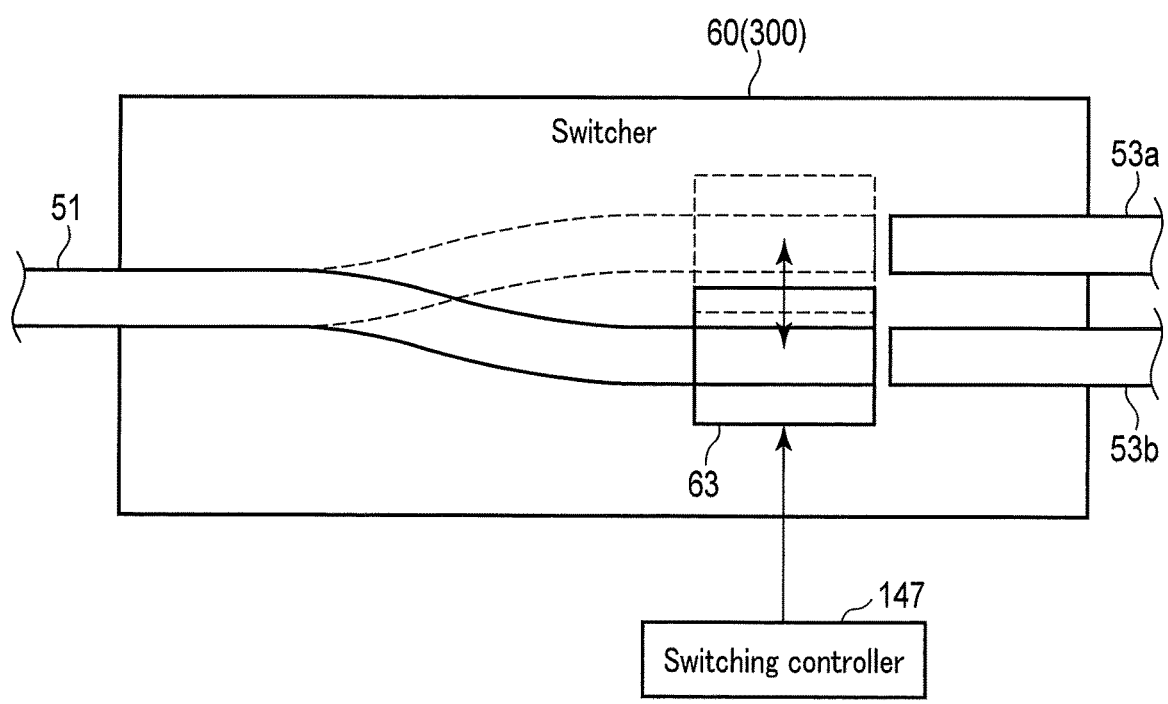
FIG. 12 is a diagram schematically showing an example of the configuration of the switcher.

As shown in FIG. 12, for example, the switcher 60 may include a drive member 63 such as an actuator disposed at an end of the light guide 51. The drive member 63 is disposed in parallel to the light guide 51. The drive member 63 relatively moves an exit end of the light guide 51 toward the light guide 53a or light guide 53b by control of the switching controller 147. The drive member 63 can stop the light guide 51 in the first state or second state by the control of the switching controller 147. In the first state, the light guide 51 is optically connected to the light guide 53a and causes the primary light to travel toward the light guide 53a side. In the second state, the light guide 51 is optically connected to the light guide 53b and causes the primary light to travel toward the light guide 53b side. Here, all of the primary light enters the light guide 53a or light guide 53b. Note that a drive amount may be adjusted, and the light guide 51 may be arranged so as to be shifted from the light guide 53a or light guide 53b. Accordingly, part of the primary light enters the light guide 53a or light guide 53b.

Although not shown, for example, the switcher 60 may include an optical component, such as a lens or a prism, and a drive member, such as an actuator, configured to drive the optical component. The drive member drives the optical component and switches the traveling direction of the primary light to the light guide 53a or light guide 53b. The switcher 60 like this is a mechanical switch.

The switcher 60 may include an optical switch configured to switch a traveling destination of the primary light to any of optical fibers optically connected to the respective illuminators 71a and 71b. Such an optical switch is an electronic optical switch using, for example, an electric engineering effect or a thermo-optic effect.

Figure 13:
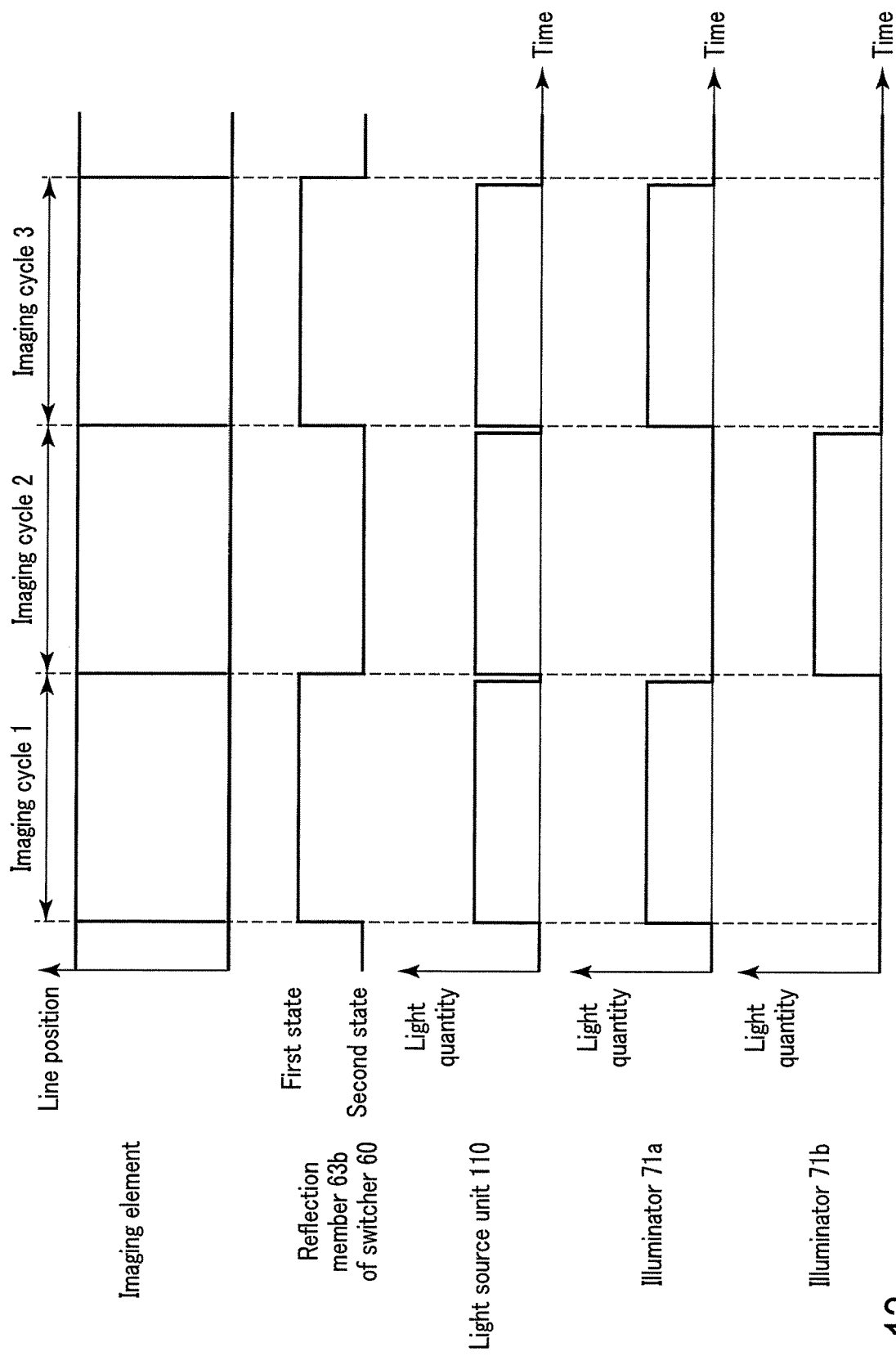
FIG. 13 is an example of a timing chart showing relationships among operation timings of an imaging element that is a CCD, the reflection member of the switcher, the light source, and the two illuminators.
Figure 14:
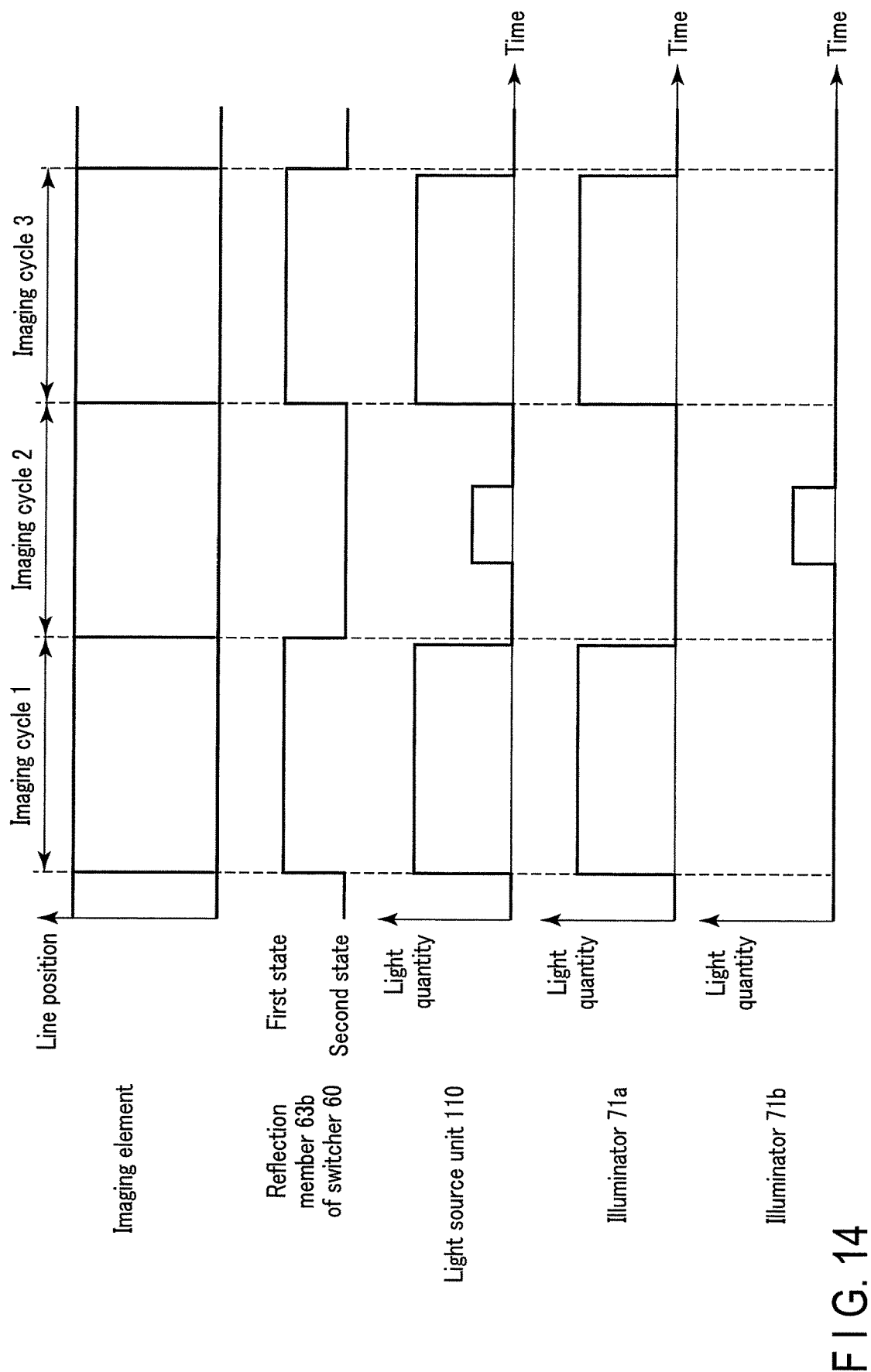
FIG. 14 is an example of a timing chart in which a light quantity and an illumination time of one illumination light are changed in the timing chart shown in FIG. 13 in order to adjust luminance distribution.

The imaging element is not limited to a rolling shutter CMOS and may include a global shutter CCD or the like. FIGS. 13 and 14 are timing charts when the CCD is used. In FIGS. 13 and 14, an imaging cycle at a certain timing is referred to as 1, 2, 3, . . . . In FIGS. 13 and 14, for simplification of illustration, only the imaging cycles 1, 2, and 3 are shown.

In FIG. 13, the switcher 60 switches the traveling direction of the primary light to either the light guide 53a or light guide 53b for each imaging cycle 1, 2, 3, . . . of the imaging element. In particular, the reflection member 63b of the switcher 60 switches to the first state at a timing when the imaging cycles 1 and 3 start. In the imaging cycles 1 and 3, the reflection member 63b remains stationary in the first state. The reflection member 63b switches to the second state at a timing when the imaging cycle 2 starts. In the imaging cycle 2, the reflection member 63b remains stationary in the second state. The light source 110 emits the primary light having a desired light quantity in the imaging cycle 1, 2, 3, . . . . In particular, at the light sources 111B, 111G, and 111R, the primary light is simultaneously emitted, and the light quantities of the primary light are the same as each other. Consequently, the light quantity of the illumination light A is the same as the light quantity of the illumination light B.

Taking heat generation of the switcher 60 and power consumption of the light source 110 into consideration, it is preferable that the light source 110 stops during switching work and the primary light is not emitted. The primary light may be continuously emitted without interruption when the switcher 60 performs switching work.

In this example, the illumination light A is emitted in the imaging cycles 1 and 3, and the illumination light B is emitted in the imaging cycle 2. The imaging element transmits the reflection light from the observation object obtained in each cycle of the imaging cycles 1, 2, 3, . . . as an electric signal to the image processor 130 through the imaging cable 85. The image processor 130 applies image processing to the electrical signal to generate to image information 1, 2, 3, . . . . The image processor 130 combines two by two from the image information 1, 2, 3, . . . to generate an image. That is, the image processor 130 combines images obtained from plural respective imaging frames within a cycle in which plural imaging frames of the imager 83 is set as one cycle to generate an image. The image processor 130 performs correction such as enhancement processing and color correction processing on the composite image. Then, the display device 200 displays the corrected image.

FIG. 14 is a timing chart in which the light quantity and illumination time of the illumination light B of the illuminator 71b are changed in the timing chart shown in FIG. 13 in order to adjust the luminance distribution. When FIG. 14 is compared with FIG. 13, the system controller 143 controls the light source controller 145 in the imaging cycles 1 and 3 to adjust the luminance distribution, and by this control, the light quantity of the primary light emitted from the light source 110 increases, and the light quantity of the illumination light A of the illuminator 71a increases. Thereby, brightness in the imaging cycles 1 and 3 increases. In addition, the system controller 143 controls the light source controller 145 in the imaging cycle 2 to adjust the luminance distribution, by this control, a light emission time (operation time) of the light source 110, which is an emission time of the primary light, shortens. In addition, the light quantity of the primary light emitted from the light source 110 decreases and the light quantity of the illumination light B decreases. Thereby, brightness in the imaging cycle 2 decreases. The adjuster 300, which is the light source controller 145, adjusts the multiplication light quantity ratio within the unit time within the imaging cycle of the imager 83 to a desired value in a cycle in which plural imaging frames of the imager 83 are set as one cycle.

In the same manner when the imaging element includes a CMOS, brightness in the imaging cycle is a multiplication value of the illumination time of the illumination light, which is the emission time of the primary light at the light source 110, by the light quantity of the illumination light, which is the light quantity of the primary light at the light source 110. In FIG. 14, the multiplication value is adjusted by adjustment of both illumination time and light quantity, and the luminance distribution is adjusted by the adjustment of the multiplication value. Note that the multiplication value, in other words, the luminance distribution only needs to be adjusted by at least one of the illumination time and light quantity.

Thereby, in this example, as in the CMOS, the luminance in the outside region can be fallen within the target luminance region, and the luminance distribution in the luminance adjustment region can be substantially uniformed over the entire image and fall within the target luminance region.

Although in the embodiment, two illuminators 71a and 71b are disposed, plural illuminators are supposed to be disposed. As shown in FIGS. 15 and 16, for example, four illuminators 71a, 71b, 71c, and 71d may be disposed. As shown in FIG. 15, the illuminators 71a, 71b, 71c, and 71d are disposed at different positions from each other on the distal end plane of the distal hard section. The four illuminators 71a, 71b, 71c, and 71d may be disposed around the imager 83. For example, the four illuminators 71a, 71b, 71c, and 71d may be disposed in a concentrically around the imager 83. As shown in FIG. 16, the endoscope 20 is optically connected to the switcher 60 and includes light guides 53a, 53b, 53c, and 53d optically connected to the illuminators 71a, 71b, 71c, and 71d, respectively. The switcher 60 only needs to switch the traveling direction of the primary light to any one of the light guides 53a, 53b, 53c, and 53d. For example, the switcher 60 is disposed at the distal end of the insertion section 30.

FIG. 17 is a diagram showing positional relationships between illuminated regions 501a, 501b, 501c, and 501d of illumination light A, B, C, and D emitted from the illuminators 71a, 71b, 71c, and 71d on the observation object away from the distal end plane by a certain distance, respectively, and the imaged region 503 of the imaging element effective for a displayed image. The illuminators 71a, 71b, 71c, and 71d are disposed at positions different from each other. Therefore, when the illuminators 71a, 71b, 71c, and 71d emit the respective illumination light A, B, C, and D to the observation object, the centers of the respective illuminated regions 501a, 501b, 501c, and 501d are shifted in the imaged region 503. The illuminators 71a, 71b, 71c, and 71d sequentially emit the illumination light A, B, C, and D in each exposure period of the imaging element, respectively. In this case, the image processor 130 combines image information four by four to generate an image. The image processor 130 performs correction such as enhancement processing and color correction processing on the composite image. Then, the display device 200 displays the corrected image.

In the same manner as the embodiment, the multiplication value is adjusted by adjustment of both illumination time and light quantity, and the luminance distribution is adjusted by the adjustment of the multiplication value. Note that the multiplication value, in other words, the luminance distribution only needs to be adjusted by at least one of the illumination time and light quantity. Thereby, in this example, the luminance distribution in the luminance adjustment region can be substantially uniformed over the entire image and fall within the target luminance region.

When the endoscope 20 of the embodiment is a side-viewing type, the illuminators 71a and 71b are disposed on a peripheral surface of the distal hard section, and the illumination light only needs to be emitted to the side. In addition, the illuminator 71a may be disposed on the distal end plane and the illuminator 71b may be disposed on the peripheral surface. Thereby, the endoscope 20 can have both front-viewing type and side-viewing type.

The illuminated regions 501a, 501b, 501c, and 501d do not need to be evenly allocated to the imaged region 503 as shown FIGS. 4 and 17. For example, it is assumed that the illuminators 71a, 71b, 71c, and 71d emit the illumination light A, B, C, and D having light distribution angles different from each other, respectively. For example, the light distribution of the illumination light A, B, C, and D may be adjusted so that the center of any one of the illuminated regions 501a, 501b, 501c, and 501d is disposed in the central part of the imaged region 503 and the intensity of the remaining illuminated region is distributed over a wide range of the imaged region 503. Thereby, difference between brightness of the central part of the imaged region 503 and brightness of the peripheral part of the central part is appropriately adjusted, and the distribution of brightness of the illumination light with respect to the imaged region 503 is appropriately adjusted.

In the embodiment, the adjustment of the adjuster 300 is not limited to the emission time of the primary light at the light source 110, the light quantity of the primary light at the light source 110, and the switching time of the switcher 60. The adjuster 300 may adjust the light quantity of the primary light traveling on the traveling path. Accordingly, as shown in FIGS. 18 and 19, the adjuster 300 may include an attenuator 301 configured to attenuate the primary light on the traveling path.

Figure 18:
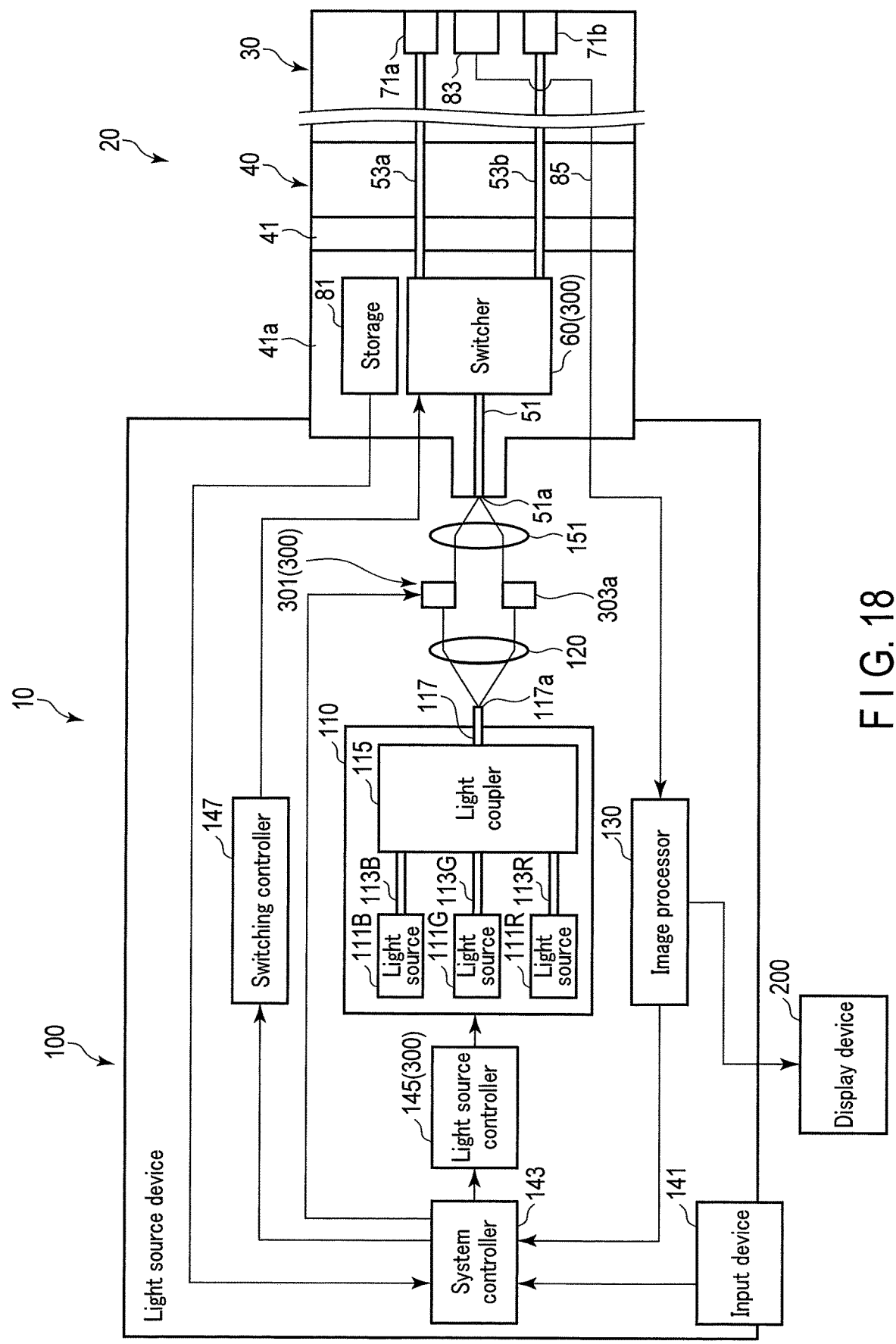
FIG. 18 is a diagram schematically showing an example of the configuration of the endoscope system.

As shown in FIG. 18, for example, the attenuator 301 may be disposed in the light source device 100. For example, the attenuator 301 may be disposed between the light source 110 and switcher 60 on the traveling path, in particular, between the first converging member 120 and endoscope side entrance end 51a. The attenuator 301 may include, for example, a variable diaphragm 303a. For the variable diaphragm 303a, an opening/closing (aperture) amount of the variable diaphragm 303a is controlled by the system controller 143, and the light quantity of the primary light that passes through the variable diaphragm 303a is controlled according to the opening/closing amount. The variable diaphragm 303a controls the light quantity of the primary light on the traveling path according to the opening/closing amount. In other words, the system controller 143 adjusts the light quantity of the primary light radiated to the illuminators 71a and 71b by adjusting the opening/closing amount of the variable diaphragm 303a, which is an attenuation rate of the attenuator 301.

The light source device 100 may include a fourth converging member 151 that is disposed between the variable diaphragm 303a and endoscope side entrance end 51a, and is configured to converge the primary light that has passed through the variable diaphragm 303a to the endoscope side entrance end 51a. The fourth converging member 151 includes, for example, a lens.

Figure 19:
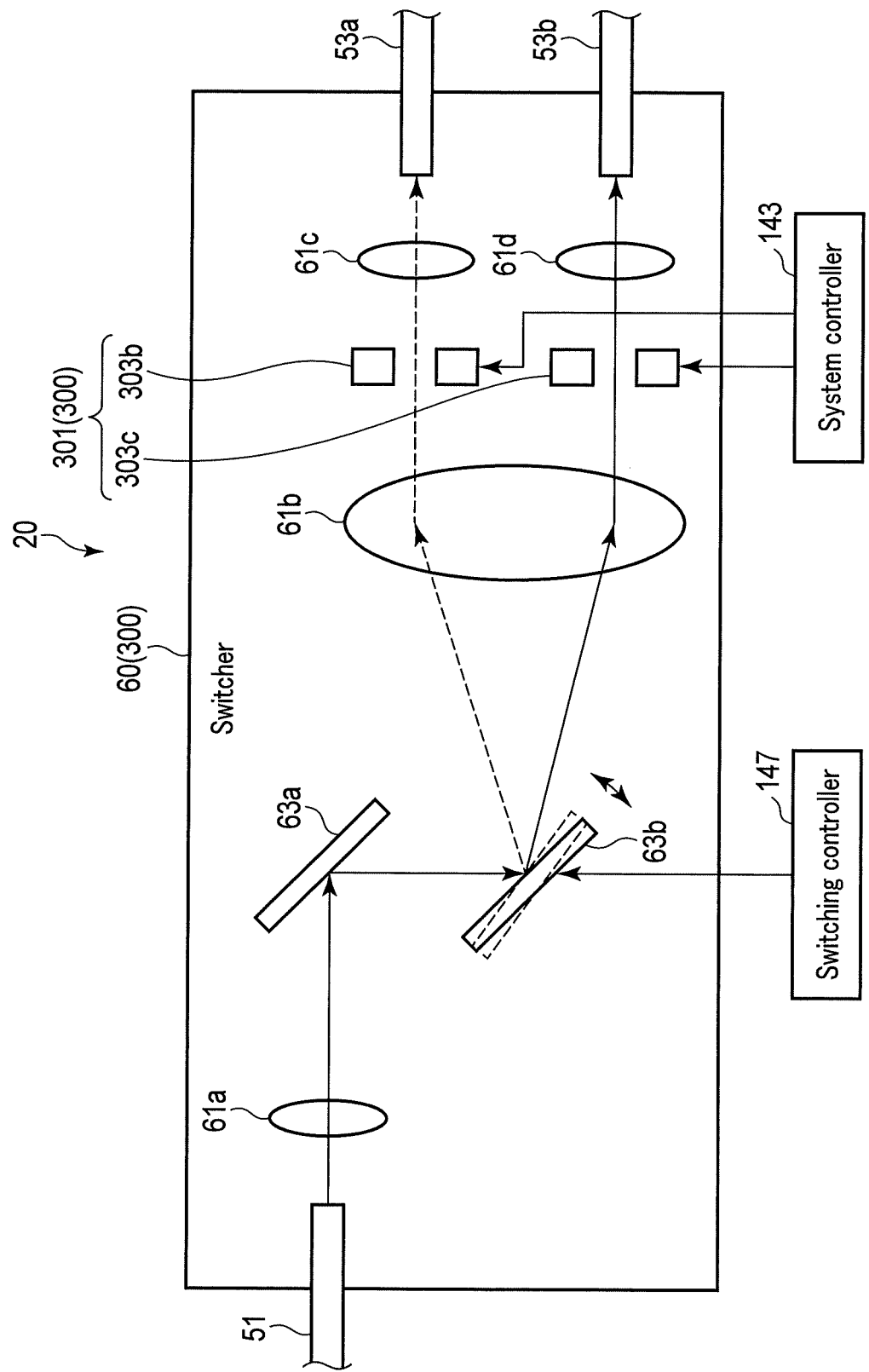
FIG. 19 is a diagram schematically showing an example of a configuration of a switcher shown in FIG. 18.

As shown in FIG. 19, for example, the attenuator 301 may be disposed in the switcher of the endoscope 20. For example, the attenuator 301 may be disposed between the reflection member 63b of the switcher 60 and the illuminators 71a and 71b on the traveling path, in particular, between the second lens 61b and third lens 61c and between the second lens 61b and fourth lens 61d. The attenuator 301 includes a variable diaphragm 303b disposed between the second lens 61b and third lens 61c, and a variable diaphragm 303c disposed between the second lens 61b and fourth lens 61d. The opening/closing (aperture) amounts of the respective variable diaphragms 303b and 303c are independently controlled by the system controller 143, and the amounts of the primary light passing through the variable diaphragms 303b and 303c are controlled in accordance with the opening/closing amounts. The variable diaphragms 303b and 303c each control the light amount of the primary light on the traveling path in accordance with the opening/closing amount.

The endoscope system 10 does not need to include both of the configuration shown in FIG. 18, that is, the variable diaphragm 303a and the configuration shown in FIG. 19, that is, the variable diaphragms 303b and 303c, and only needs to include at least one configuration.

The attenuator 301 may function as the reflection member 63b whose state is controlled by the switching controller 147. This state indicates, for example, an inclination of the reflection member 63b with respect to the central axis of the primary light emitted from the light guide 51. The reflection member 63b may reflect at least part of the primary light radiated to the reflection member 63b toward the light guide 53a side or light guide 53b side by the inclination of the reflection member 63b. In particular, the reflection member 63b may reflect the primary light so that the central axis of the primary light reflected by the reflection member 63b is shifted with respect to the central axes of the light guides 53a and 53b. Thereby, the reflection member 63b may reflect at least part of the primary light radiated to the reflection member 63b toward the light guide 53a side or light guide 53b side. Accordingly, the light quantity of the primary light that enters the light guide 53a or 53b is adjusted.

The attenuator 301 may function as the third and fourth lenses 61c and 61d whose positions in the traveling direction of the primary light are controlled by the system controller 143. The third and fourth lenses 61c and 61d are disposed to be shifted with respect to the second lens 61b in the traveling direction of the primary light. Thereby, the focal positions of the third and fourth lenses 61c and 61d are adjusted and the light quantities of primary light that enters the light guides 53a and 53b are adjusted.

In these examples, the light quantities of the primary light that travels to the illuminators 71a and 71b can be adjusted by the attenuator 301.

Note that the attenuator 301 may be disposed between the light source 110 and switcher 60, adjust the attenuation rate in synchronization with operation of the switcher 60, and adjust the light quantity of the primary light traveling to the switcher 60.

Figure 20:
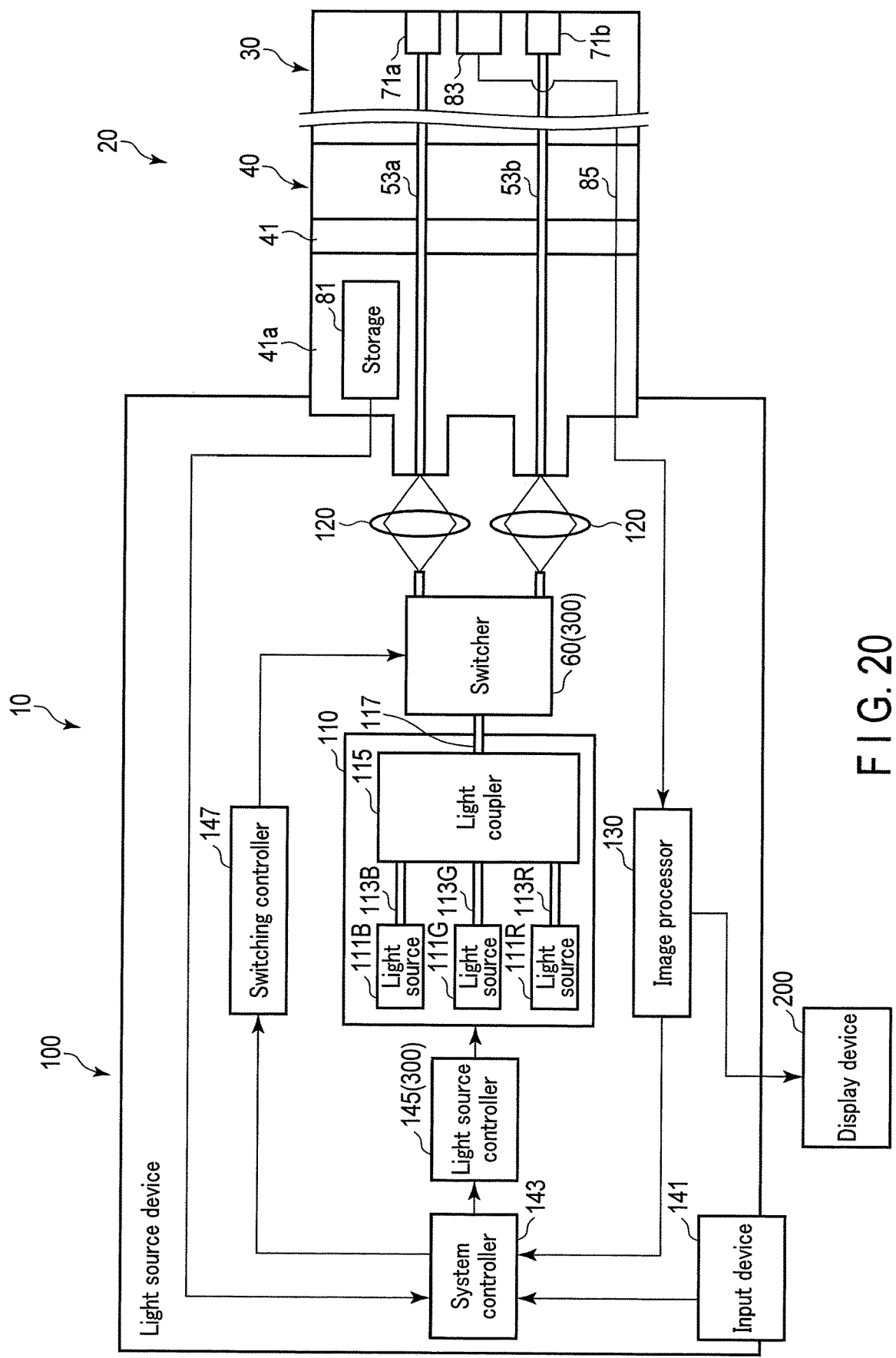
FIG. 20 is a diagram schematically showing an example of the configuration of the endoscope system.

As shown in FIG. 20, the switcher 60 may be disposed inside the light source device 100. The switcher 60 is optically connected to the light guide 117. Two first converging members 120 are disposed, and one of the first converging members 120 is disposed between the switcher 60 and light guide 53a. The other first converging member 120 is disposed between the switcher 60 and light guide 53b.

The switcher 60 switches the traveling direction of the primary light guided by the light guide 117 to either the one first converging member 120 or the other first converging member 120. The one first converging member 120 converges the primary light to the light guide 53a, and the other first converging member 120 converges the primary light to the light guide 53b.

Although not shown, the switcher 60 may be disposed between the light source device 100 and connector 41a and disposed inside an adapter configured to connect the connector 41a to the light source device 100.

Modified Example

Hereinafter, a modified example of the first embodiment will be described with reference to FIGS. 21 and 22.

The imaging element includes, for example, a rolling shutter type CMOS.

In the modified example, there are switching periods S1 and S2 both of which have a certain period in one exposure period. The switching controller 147 switches the reflection member 63b of the switcher 60 to the first state in the switching period S1. The switching controller 147 switches the reflection member 63b of the switcher 60 to the second state in the switching period S2. The light source 110 emits primary light having a desired light quantity in the switching periods S1 and S2. Emission periods of the primary light corresponding to the switching periods S1 and S2 are referred to as emission periods E1 and E2, respectively.

In a state in which the reflection member 63b stops in the first state and the light source 110 emits primary light, that is, in the switching period S1 and emission period E1, the illuminator 71a emits the illumination light A and the illuminator 71b does not emit the illumination light B. In a state in which the reflection member 63b stops in the second state and the light source 110 emits primary light, that is, in the switching period S2 and emission period E2, the illuminator 71a does not emit the illumination light A and the illuminator 71b emits the illumination light B. In any of the readout periods 1, 2, 3, . . . , since the light source 110 stops and primary light is not emitted, the illuminators 71a and 71b do not emit the illumination light A and B. Here, the adjuster 300, which is the light source controller 145, adjusts a multiplication light quantity ratio within the unit time within the exposure period of the imager 83 in a cycle in which one imaging frame of the imager 83 is set as one cycle to a desired value. The multiplication light quantity is a multiplication value of the emission time of the primary light at the light source 110 by the light quantity of the primary light at the light source 110.

The imaging element transmits reflection light from the observation object obtained in each of the emission periods E1 and E2 as an electric signal to the image processor 130 through the imaging cable 85. The image processor 130 applies image processing to the electric signal to generate image information 1 and 2. The image processor 130 combines the image information 1 and 2 to generate an image. The image processor 130 performs correction such as enhancement processing and color correction processing on the image. Then, the display device 200 displays the corrected composite image. An image obtained within one exposure period is generated from electric charges stored in a light-receiving element of the imaging element in the emission periods E1 and E2. For this reason, the generated image is the same as an image obtained by adding the illumination light A and B at a ratio between the multiplication values of the emission times by light quantities of the illumination light A and B.

Figure 21:
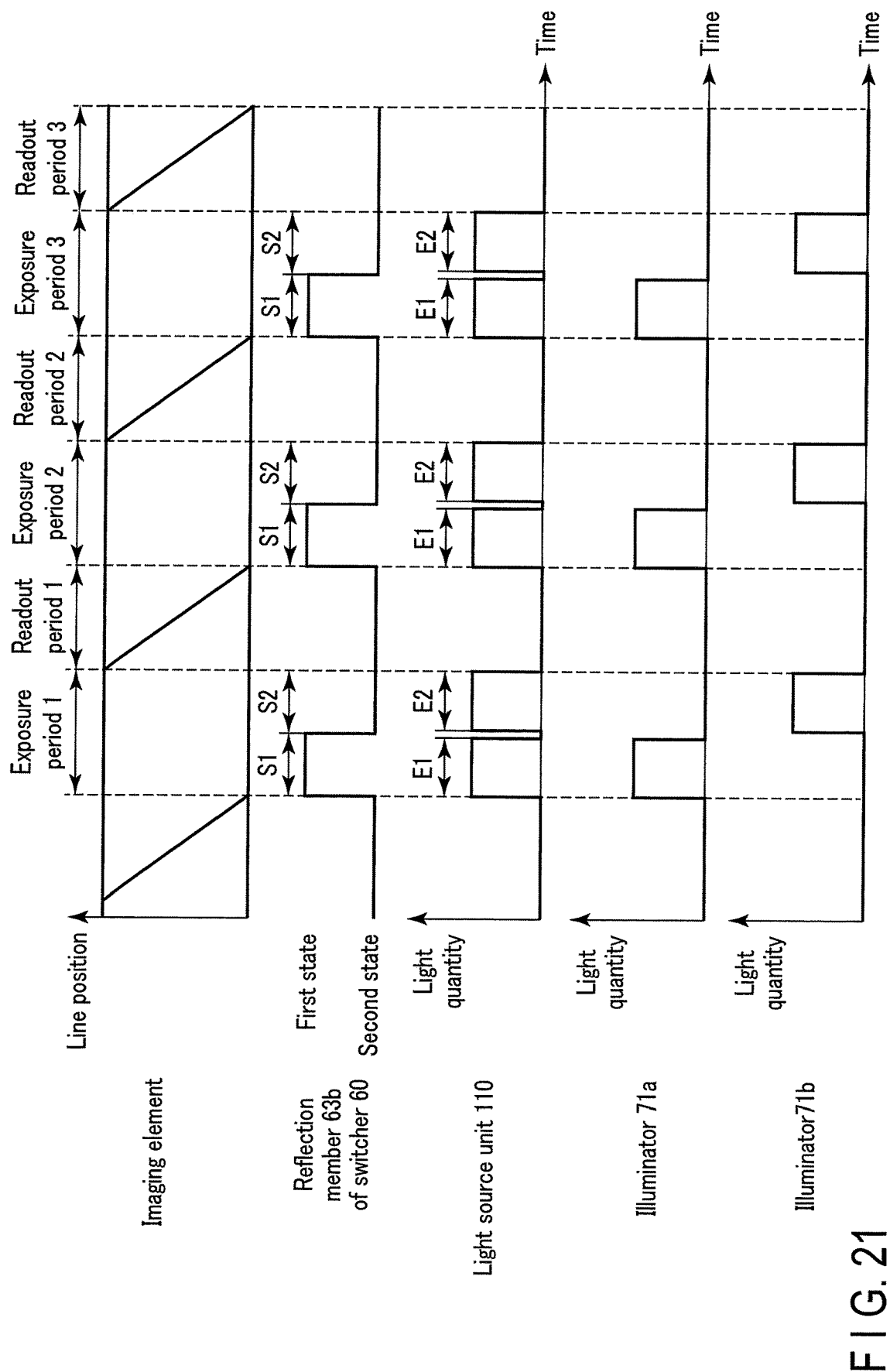
FIG. 21 is an example of a timing chart showing relationships among operation timings of the imaging element that is a CMOS, the reflection member of the switcher, the light source, and the two illuminators.
Figure 22:
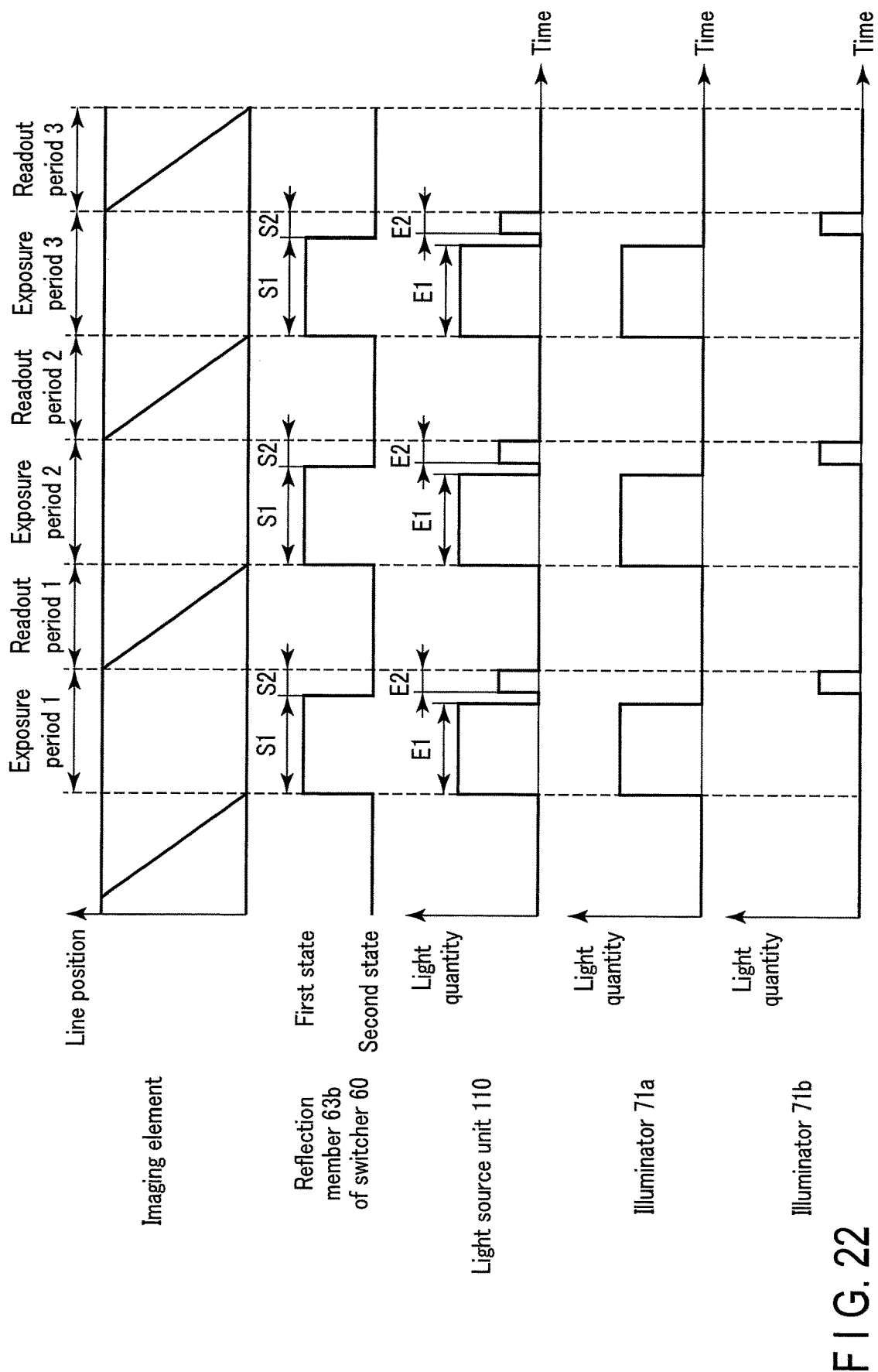
FIG. 22 is an example of a timing chart in which a switching period and an emission period are changed in the timing chart shown in FIG. 21 in order to adjust luminance distribution.

When FIG. 22 is compared with FIG. 21, the system controller 143 controls the light source controller 145 in the exposure periods 1, 2, and 3 to adjust the luminance distribution, and by this control, the light emission time (operation time) of the light source 110, which is the emission time of the primary light, in the emission period E1 becomes longer, the light quantity of the primary light emitted from the light source 110 in the emission period E1 increases, and the light quantity of the illumination light A of the illuminator 71a increases. The light emission time (operation time) of the light source 110, which is the emission time of the primary light, in the emission period E2 becomes shorter, the light quantity of the primary light emitted from the light source 110 in the emission period E2 decreases, and the light quantity of the illumination light B of the illuminator 71b decreases. Even if such control is performed, brightness in the exposure periods 1, 2, and 3 in FIG. 22 does not change with respect to the brightness in the exposure periods 1, 2, and 3 in FIG. 21.

For example, if the illuminated regions 501a and 501b of the modified example are the same as those shown in FIG. 4, the multiplication value is adjusted by the adjustment of at least one of the illumination time and light quantity of each of the illumination light A and B in the same manner as the first embodiment. By the adjustment of the multiplication value, the luminance of the outside region falls within the target luminance region, and the luminance distribution in the luminance adjustment region is substantially uniformed over the entire image and falls within the target luminance region. Although both illumination time and light quantity may be adjusted, if resolution of light control is sufficient, only one of them may be adjusted.

In the first embodiment, since images in plural exposure periods are combined, acquisition of one display image requires a time corresponding to the plural exposure periods. In the modified example, since the adjustment is made in one exposure period, a frame rate can be increased and blurring of the composite image due to a time difference between the imager 83 and observation object can be reduced.

Switching of illumination does not need to be performed within one exposure period. For example, when four illuminators are disposed, the illuminators may be switched to two illuminators in each of the exposure periods 1 and 2, and images in the exposure periods 1 and 2 may be combined to generate a display image.

Second Embodiment

Figure 23:
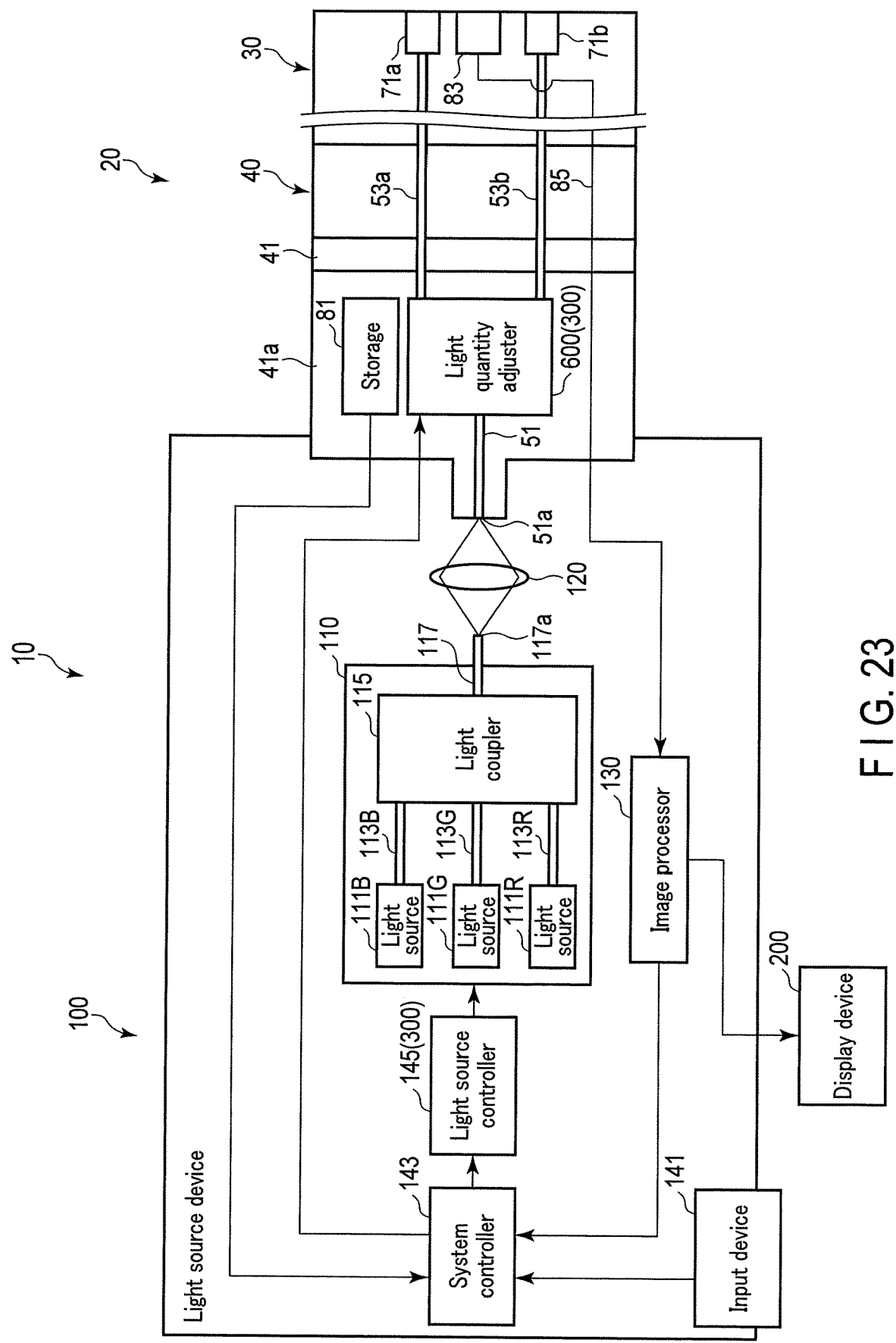
FIG. 23 is a diagram schematically showing an example of a configuration of an endoscope system according to a second embodiment of the present invention.

Hereinafter, a second embodiment of the present invention will be described with reference to FIGS. 23 and 24. In the embodiment, only differences from the first embodiment will be described.

An adjuster 300 includes a light quantity adjuster 600 instead of the switcher 60. The light quantity adjuster 600 includes a splitter 307 configured to split primary light according to a desired ratio. The splitter 307 is disposed, for example, in a connector 41a. The splitter 307 is optically connected to a light guide 51. The splitter 307 is optically connected to a light guide 53a side by a light guide 53e and is optically connected to a light guide 53b side by a light guide 53f. The light guides 53e and 53f are, for example, optical fibers.

The splitter 307 splits primary light so that a ratio between light quantities of the primary light that travels to the respective light guides 53e and 53f is, for example, 1:1. Note that the ratio between the light quantities after split may be desirably adjusted according to light conversion characteristics or the like of illuminators 71a and 71b.

Between the light guide 53e and light guide 53a, a fifth lens 61e, a variable diaphragm 303b of an attenuator 301, and a third lens 61c are disposed in this order. Between the light guide 53f and light guide 53b, a sixth lens 61f, a variable diaphragm 303c of the attenuator 301, and a fourth lens 61d are disposed in this order. The attenuator 301 attenuates the primary light split by the splitter 307.

The primary light guided by the light guide 53e is converted into substantially parallel light by the fifth lens 61e and is thinned by the variable diaphragm 303b. Then, the primary light is converged to the light guide 53a by the third lens 61c and is guided to an illuminator 71a by the light guide 53a. The primary light guided by the light guide 53f is converted into substantially parallel light by the sixth lens 61f and is thinned by the variable diaphragm 303c. Then, the primary light is converged to the light guide 53b by the fourth lens 61d and is guided to an illuminator 71b by the light guide 53b.

In the embodiment, as in the first embodiment, the illuminators 71a and 71b radiate illumination light A and B toward regions different from each other, respectively. A system controller 143 adjusts a multiplication light quantity ratio within a unit time by adjusting an attenuation rate of the attenuator 301. The system controller 143 may control the attenuation rate on the basis of storage information stored in a storage 81. Adjustment of opening/closing amounts of the variable diaphragms 303b and 303c can adjust the light quantities of primary light travelling to the illuminators 71a and 71b, respectively. Then, luminance of an outside region can be fallen within a target luminance region, and a luminance distribution in a luminance adjustment region can be substantially uniformed over the entire image and can be fallen within the target luminance region.

The splitter 307 may use, for example, a spatial optical system using a half mirror or the like. The attenuator 301 may adjust positions in directions orthogonal to central axes of the third and fourth lenses 61c and 61d and an angle of an optical member (for example, a mirror or a glass window) separately disposed in a light path. Thereby, the central axes of the primary light traveling to the light guides 53a and 53b are shifted with respect to the central axes of the light guides 53a and 53b, and light quantities of the primary light that enters the light guides 53a and 53b are adjusted. Accordingly, the luminance of the outside region can be fallen within the target luminance region, and the luminance distribution in the luminance adjustment region can be substantially uniformed over the entire image and can be fallen within the target luminance region.

Note that the invention of the present application is not limited to the above embodiments and can be variously modified in a range not departing from the gist in an implementation stage. In addition, the embodiments may be implemented in appropriate combinations as much as possible, and in that case, combined effects are obtained. Furthermore, the above embodiments include inventions at various stages, and various inventions can be extracted by appropriate combinations of plural constituent elements disclosed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
   a light source configured to emit primary light;
   a first illuminator configured to illuminate first illumination light to an observation object, the first illumination light being based on the primary light;
   a second illuminator configured to illuminate second illumination light to the observation object, the second illumination light being based on the primary light, wherein centers of illuminated regions on the observation object, illuminated by the first illumination light and the second illumination light, respectively, are at positions different from each other;
   an imager configured to perform imaging using reflection light from the observation object illuminated with the first illumination light and the second illumination light;
   an image processor configured to generate an image based on a signal from the imager;
   an adjuster configured to distribute the primary light to the first illuminator and the second illuminator; and
   a system controller configured to control the adjuster to adjust a ratio of distributing the primary light to the first illuminator and the second illuminator, so that a luminance distribution in the image generated according to the reflection light from the observation object illuminated with the first illumination light and the second illumination light approaches a target luminance distribution;
   wherein the image includes a luminance adjustment region adapted to change a luminance according to adjustment of the ratio of distributing the primary light to the first illuminator and the second illuminator, the luminance adjustment region comprising a target luminance region having a target luminance and an outside region different from the target luminance region, and
   the system controller is configured to control the ratio through the adjuster so that a luminance in the outside region is changed to fall within the target luminance in the target luminance region, when the image includes the outside region.

2. The endoscope system according to claim 1, wherein the adjuster is configured to distribute a multiplication light quantity per unit time relating to imaging processing of the imager to the first illuminator and the second illuminator.

3. The endoscope system according to claim 2, wherein:
   the adjuster includes a switcher that is disposed on a traveling path of the primary light that travels from the light source to the first and second illuminators and is configured to switch a traveling direction of the primary light to the first illuminator or the second illuminator; and
   the system controller is configured to adjust a switching time of the switcher and adjust a multiplication light quantity ratio within a unit time by adjusting the switching time within the unit time, wherein:
   the multiplication light quantity is a multiplication value of an illumination time of one illumination light by a light quantity of the one illumination light; and
   the multiplication light quantity ratio is a ratio between the multiplication light quantity of the first illumination light and the multiplication light quantity of the second illumination light.

4. He endoscope system according to claim 3, wherein:
   the adjuster is configured to adjust the light quantity of the primary light radiated to the first illuminator or the second illuminator; and
   the system controller is configured to adjust the multiplication light quantity ratio by adjusting, through the adjuster, a combination of a radiation time of the primary light radiated to the first illuminator or the second illuminator and the light quantity of the primary light radiated to the first illuminator or the second illuminator.

5. The endoscope system according to claim 4, wherein:
   the adjuster includes a light source controller that is configured to control the light source in order to adjust the light quantity of the primary light emitted from the light source; and
   the system controller is configured to adjust the light quantity of the primary light radiated to the first illuminator or the second illuminator by adjusting the light quantity of the primary light at the light source in synchronization with switching by the switcher through the light source controller.

6. The endoscope system according to claim 4, wherein:
   the adjuster includes an attenuator that is disposed between the switcher and the first illuminator or the second illuminator on the traveling path and is configured to attenuate the primary light; and
   the system controller is configured to adjust the light quantity of the primary light radiated to the first illuminator or the second illuminator by adjusting an attenuation rate of the attenuator.

7. The endoscope system according to claim 3, further comprising an endoscope and a light source device connected to the endoscope, wherein:

the first illuminator or the second illuminator are disposed in the endoscope;

the light source is disposed in the light source device, and includes a laser diode;

a light guide that is disposed on the traveling path and is configured to guide the primary light includes single-core optical fibers; and the switcher includes an optical switch that is configured to switch a traveling destination of the primary light to any of the optical fibers optically connected to the first illuminator and the second illuminator.

8. The endoscope system according to claim 7, wherein the endoscope includes the switcher, the imager, and a storage that is configured to store optical characteristics of the endoscope and imaging characteristics of the imager, and the system controller is configured to control the switcher based on storage information stored in the storage.

9. The endoscope system according to claim 2, further comprising an endoscope and a light source device connected to the endoscope, wherein the adjuster includes:

a splitter that is configured to split the primary light at the adjusted ratio; and an attenuator that is configured to attenuate the primary light split by the splitter, wherein:

the light source device includes a system controller that is configured to control the light source and the attenuator; and the system controller is configured to adjust a multiplication light quantity ratio within a unit time by adjusting an attenuation rate of the attenuator, wherein:

the multiplication light quantity is a multiplication value of an illumination time of one illumination light by a light quantity of the one illumination light; and the multiplication light quantity ratio is a ratio between the multiplication light quantity of the first illumination light and the multiplication light quantity of the second illumination light.

10. The endoscope system according to claim 9, wherein the endoscope includes the splitter, the attenuator, the imager, and a storage that is configured to store optical characteristics of the endoscope and imaging characteristics of the imager, and the system controller is configured to control the attenuation rate based on storage information stored in the storage.

11. The endoscope system according to claim 2, wherein:

the adjuster is configured to adjust a multiplication light quantity ratio within a unit time in an exposure period of the imager to a value in a cycle in which plural imaging frames of the imager are set as one cycle; and the image processor is configured to combine images obtained from the respective imaging frame in the cycle to generate the image, wherein:

the multiplication light quantity is a multiplication value of an illumination time of one illumination light by a light quantity of the one illumination light; and the multiplication light quantity ratio is a ratio between the multiplication light quantity of the first illumination light and the multiplication light quantity of the second illumination light.

12. The endoscope system according to claim 2, wherein the adjuster is configured to adjust a multiplication light quantity ratio within a unit time in an exposure period of the imager to a value in a cycle in which one imaging frame of the imager is set as one cycle, wherein:

the multiplication light quantity is a multiplication value of an illumination time of one illumination light by a light quantity of the one illumination light; and the multiplication light quantity ratio is a ratio between the multiplication light quantity of the first illumination light and the multiplication light quantity of the second illumination light.

13. The endoscope system according to claim 1, wherein the system controller is configured to decrease a light quantity of the first illumination light if increasing the light quantity of the first illumination light through the adjuster increases a size of the outside region or a maximum luminance in the outside region.

14. The endoscope system according to claim 1, further comprising a storage that is configured to store optical characteristics of the first illumination light and the second illumination light in the luminance adjustment region and a weighting factor affecting luminance of the image, wherein the system controller is configured to control a light quantity ratio of the illumination light through the adjuster based on the weighting factor.

15. The endoscope system according to claim 1, wherein the system controller is configured to set an adjustment excluding region in the image, the adjustment excluding region including a metal colored object or a linear artifact and excluded from a subject of luminance adjustment to the target luminance.

16. The endoscope system according to claim 1, further comprising an endoscope and a light source device connected to the endoscope, wherein:

the adjuster is disposed on a traveling path of the primary light that travels from the light source to the first illuminator and the second illuminator;

a light guide that is disposed on a traveling path from the light source to the adjuster and is configured to guide the primary light is shared by traveling paths from the light source to the first illuminator and the second illuminator; and the first illuminator and the second illuminator each include a light converter that is configured to convert at least part of the primary light into the illumination light that is secondary light having an optical characteristic different from an optical characteristic of the primary light.

17. The endoscope system according to claim 16, wherein the endoscope includes a connector connected to the light source device, and the connector includes the light guide that is configured to optically connect the light source and the adjuster.

18. An endoscope system comprising:

a light source configured to emit primary light;

a first illuminator material configured to illuminate first illumination light to an observation object, the first illumination light being based on the primary light;

a second illuminator material configured to illuminate second illumination light to the observation object, the second illumination light being based on the primary light, wherein centers of illuminated regions on the observation object, illuminated by the first illumination light and the second illumination light, respectively, are at positions different from each other;

an image sensor configured to perform imaging using reflection light from the observation object illuminated with the first illumination light and the second illumination light; and a controller configured to:
  generate an image based on a signal from the image sensor;
  control distribution of the primary light to the first illuminator material and the second illuminator material; and
  control an adjustment of a ratio of distributing the primary light to the first illuminator material and the second illuminator material, so that a luminance distribution in the image generated according to the reflection light from the observation object illuminated with the first illumination light and the second illumination light approaches a target luminance distribution;

wherein the image includes a luminance adjustment region adapted to change a luminance according to adjustment of the ratio of distributing the primary light to the first illuminator material and the second illuminator material, the luminance adjustment region comprising a target luminance region having a target luminance and an outside region different from the target luminance region, and the controller is configured to control the adjustment of the ratio so that a luminance in the outside region is changed to fall within the target luminance in the target luminance region, when the image includes the outside region.

* * * * *